United States Patent [19]

Heim et al.

[11] Patent Number: 5,126,134
[45] Date of Patent: Jun. 30, 1992

[54] PHARMACEUTICALLY ACTIVE COMBINATION

[75] Inventors: Jutta Heim, Ramlinsburg, Switzerland; Giancarlo Agnelli, Perugia, Italy; Czeslaw Czendlik, Bubendorf, Switzerland

[73] Assignees: Ciba-Geigy Corporation, Ardsley, N.Y.; UCP Gen-Pharma AG, Kirchberg, Switzerland

[21] Appl. No.: 408,836

[22] Filed: Sep. 18, 1989

[30] Foreign Application Priority Data

Sep. 21, 1988 [GB] United Kingdom ............... 8822147

[51] Int. Cl.$^5$ .................... A61K 37/547; A61K 37/02
[52] U.S. Cl. .............................. 424/94.64; 424/94.63; 514/2; 514/12
[58] Field of Search .......................... 424/94.63, 94.64; 514/2.21

[56] References Cited

U.S. PATENT DOCUMENTS 4,801,576  1/1989  Fritz et al. ........................ 514/12
4,944,943  7/1990  Eschenfelder et al. .......... 424/94.64

FOREIGN PATENT DOCUMENTS 0181267  5/1986  European Pat. Off. .
41766  8/1988  European Pat. Off. .
3804600  8/1989  Fed. Rep. of Germany .

OTHER PUBLICATIONS

J. M. Stassen et al., F. K. Schattauer Verlag (Stuttgart) 58(3) 947-950 (1987)-Thromb. Haemost.
F. Markwardt, Cardiovascular Pharmacology (1987) J. Gy. Papp (ed)-pp. 449-456.
Tamao et al., Thrombosis and Haemostasis 56(1), 28-34, (1986).
Markwardt et al., Thrombosis and Haemostasis 47(3), 226-229 (1982).
Rijken et al., Bioichem. J. (1986), 238, 643-646.
Van Zonneveld et al., J. Cell. Biochem. 32:169-178 (1986).
Ehrlich et al., Fibrinolysis, vol. 1, No. 2 (1987) pp. 75-82.
Haber et al., Science, vol. 243 (Jan. 6, 1989), pp. 51-56.

*Primary Examiner*—Jacqueline Stone
*Attorney, Agent, or Firm*—Steven R. Lazar; JoAnn Villamizar

[57] ABSTRACT

There is provided a pharmaceutical composition comprising as component A a plasminogen activator and as component B hirudin together with a pharmaceutically acceptable carrier. The pharmaceutical composition can be used for the prophylaxis and therapy of thrombosis or diseases caused by thrombosis.

34 Claims, 4 Drawing Sheets

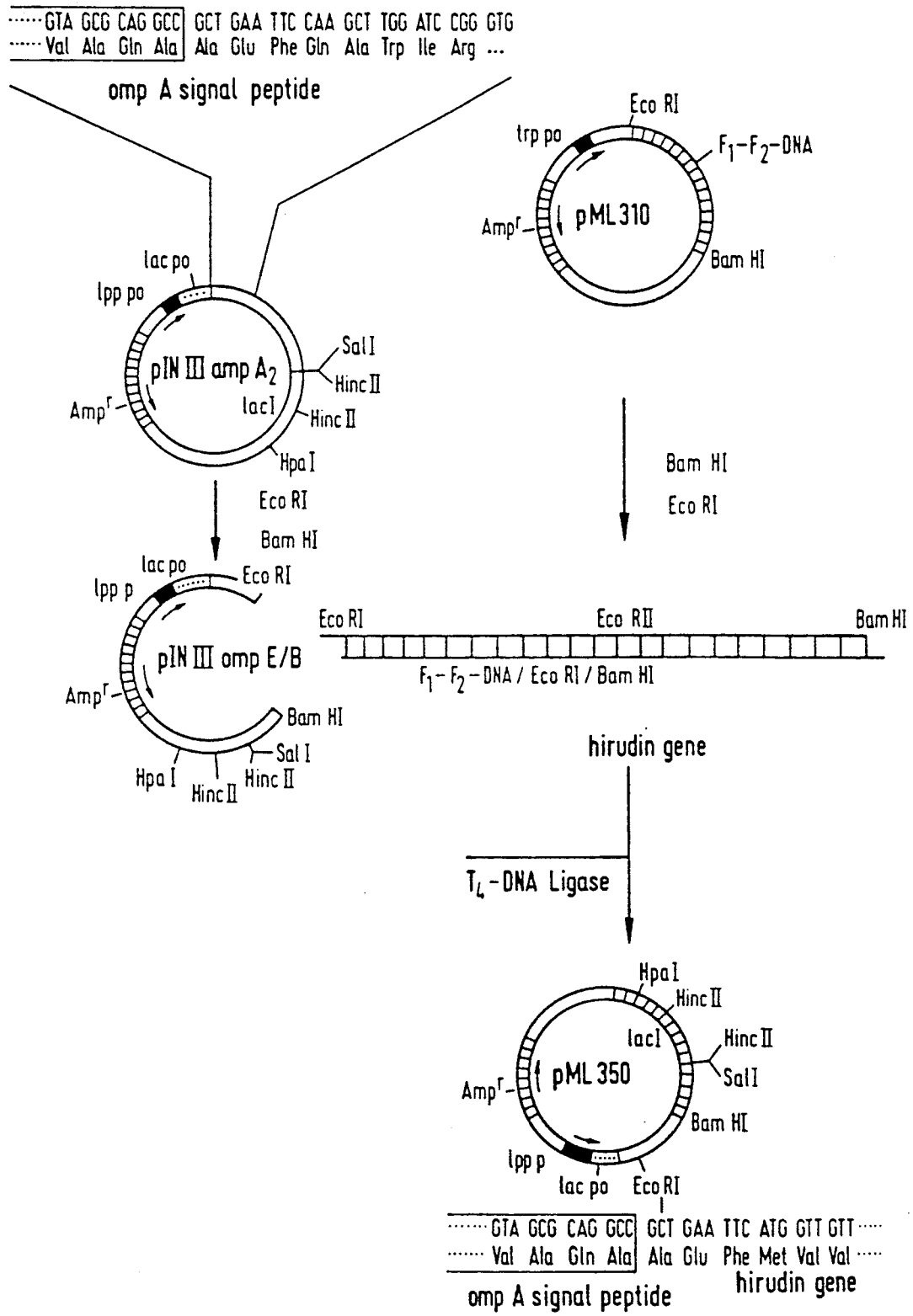

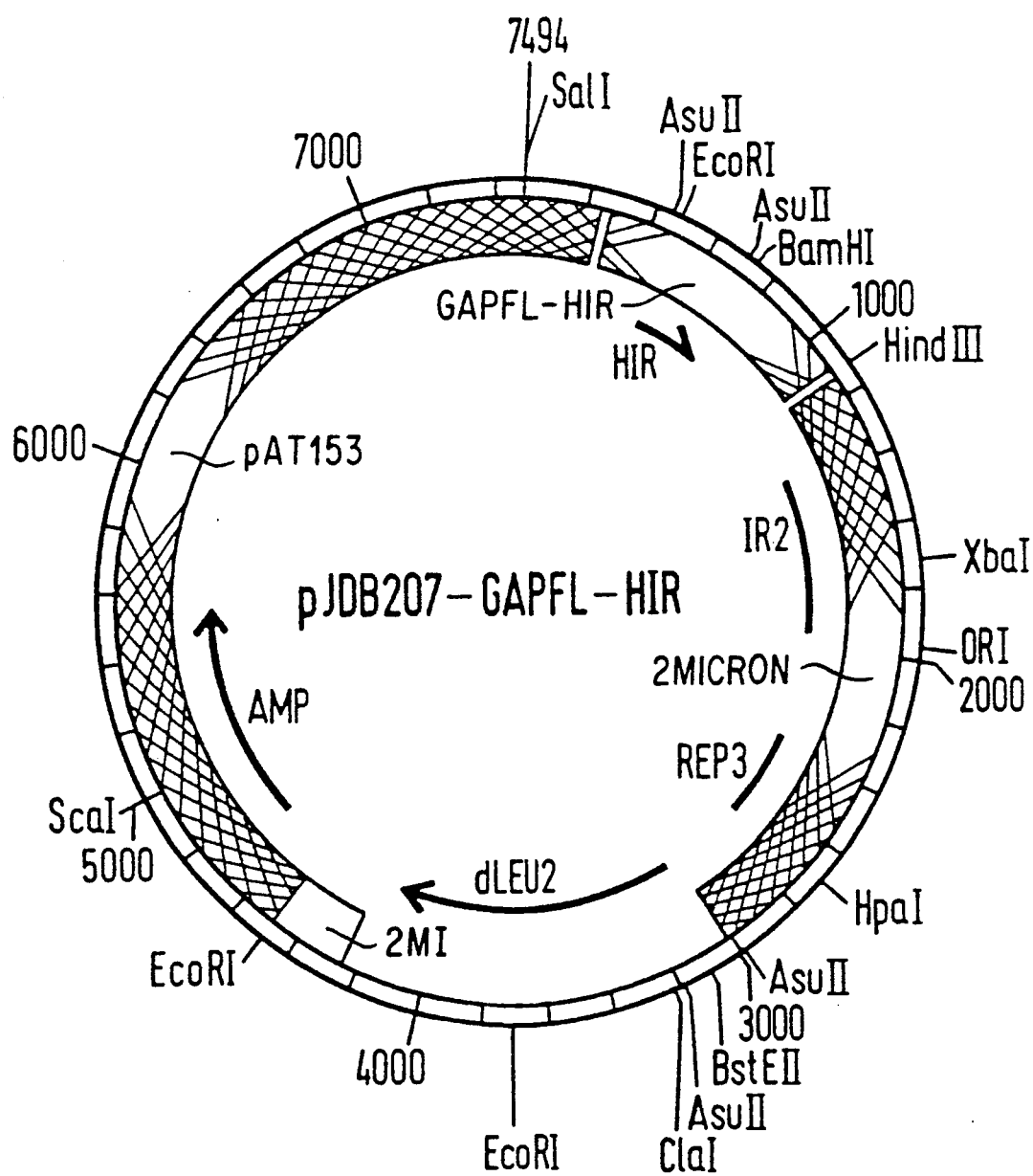
FIG. 4  Plasmid map of plasmid pJDB207/GAPFL-HIR

PHARMACEUTICALLY ACTIVE COMBINATION

The invention relates to pharmaceutical compositions comprising a combination of a plasminogen activator and a thrombin inhibitor and to the use of said compositions for the prophylaxis or therapy of coagulation disorders.

Mammalian plasma contains two enzymatic systems coexisting in a dynamic equilibrium: the coagulation system which is capable of forming blood clots and the fibrinolytic system capable of dissolving blood clots. This dynamic equilibrium ensures that clots normally form only when and where they are required to prevent loss of blood from injured vessels and that after natural repair of the injury the superfluous clots are dissolved. In cases where the fibrinolytic capacity of the body is insufficient to remove intravascular clots (thrombi), for example in patients suffering from thromboembolisms or post-surgical complications, it may be indispensable to use exogenously administered fibrinolytic (thrombolytic) agents.

One component of the fibrinolytic system is a group of enzymes named plasminogen activators, which convert the zymogen plasminogen to the proteolytic enzyme plasmin. Plasmin then degrades the fibrin network of the clots to form soluble products.

Two types of plasminogen activators (hereinafter referred to as "PAs") can be isolated from human body fluids or cells: urokinase or urokinase-type plasminogen activator (hereinafter referred to as "u-PA"), a serine protease occurring e.g. in urine and kidney cells, and tissue-type plasminogen activator (hereinafter referred to as "t-PA") which is produced by endothelial cells and found in a number of endocrine tissues.

Both t-PA and u-PA exist in two molecular forms: a single-chain form (often designated as "sct-PA" and "scu-PA", respectively) and a two-chain (tc) form. The single-chain or pro-enzyme form is converted into the two-chain form by the action of proteolytic enzymes at well-defined positions in the polypeptide sequence. The resulting two chains of the processed PA protein remain attached to each other via a sulphur-sulphur bridge. The carboxyterminal fragment or B-chain mediates the enzymatic activity of the PA whereas the aminoterminal A-chain contains regulatory units such as fibrin binding sites.

While it is generally acknowledged that t-PA and u-PA (especially scu-PA) are of utmost usefulness in thrombolytic therapy it is nevertheless observed that none of these drugs alone is sufficient for permanently opening of occluded vessels. As the reocclusion rate is extraordinary high additional therapeutical means are to be taken which exert a favourable influence on the course of disease.

Recently, thrombin inhibitors such as heparin, low molecular weight fractions of heparin or arginine derivatives (for examples argipidin) have been used in combination with plasminogen activators in anti-thrombotic therapy [cf. Y. Tamao et al., Thromb. Haemost. 56, 28–34 (1986); J. M. Stassen et al., ibid. 58, 947–950 (1987); European Patent Application No. 181,267]. The inhibition of thrombin has the following effects on the coagulation system: (1) the conversion of fibrinogen to monomeric fibrin is inhibited; (2) the maturation of factor XIII to factor XIIIa which converts soluble fibrin into the insoluble fibrin matrix, is prevented; soluble fibrin is more susceptible to proteolytic degradation by plasmin than insoluble fibrin; (3) the formation of factors Va and VIIIa (feed-back accelerators of thrombin formation) is inhibited; (4) plasminogen activator inhibitor 1 (PAI-1) is proteolytically degraded; while (5) thrombin bound in the thrombomodulin-thrombin complex is not inhibited by thrombin inhibitors; the complex can therefore continue to act as an activator of protein C which together with protein S proteolytically degrades factors Va and VIIIa (supra). The action of the plasminogen activator t-PA itself leads to local hyper-aggregability mediated by activated platelets [see R. J. Sheberski et al., Thromb. Res. 52, 381 (1988)]. Hence, thrombin inhibitors are believed to prevent the continuous formation of fibrin and the growth of thrombi by continuous deposition of newly formed fibrin. Moreover, since scu-PA is cleaved by thrombin at the $Arg^{156}$-$Phe^{157}$ bond to yield an inactive two chain form, it is inactive without concomitant administration of a thrombin inhibitor.

Also, during lysis significant amounts of fibrin are generated in circulation [Owen et al., Blood 72, 616–620 (1988); H. J. Rapold et al., Circulation 79, 980–988 (1988)]. Altogether, lysis via a plasminogen activator leads to an imbalance between thrombogenic and thrombolytic forces, locally as well as systemically, resulting in incomplete lysis of existing clots, rapid reocclusion at the same sites and novel clot formation at other predisposed sites. Anticoagulation by heparin will not prevent these side effects of lysis (Rapold, supra).

As indicated by the first results available the combined administration of plasminogen activator and thrombin inhibitor might help to overcome the reocclusion problem arising in conventional fibrinolytic plasminogen activator therapy. However, in view of the relatively small anticoagulant effects observed in the combined administration of heparin or arginine derivatives with plasminogen activators there is a need for a combination of plasminogen activator and a strong thrombin inhibitor having a more pronounced inhibitory effect on the coagulation cascade thus minimizing the reocclusion problem in fibrinolytic therapy. The combination with a strong thrombin inhibitor would also reduce the amount of the plasminogen activator required to dissolve the clot and would further decrease the time required for dissolving the clot. This is especially important when life-threatening conditions are to be managed. It is an object of the invention to provide such an improved combination for use in a combined anticoagulant/fibrinolytic treatment of coagulation disorders.

It has surprisingly been found that the dissolution of thrombi is accelerated significantly and the risk of reocclusion is considerably reduced when the fibrinolytic plasminogen activator is applied in combination with the antithrombotic agent hirudin.

Accordingly, the invention concerns a pharmaceutical combination composition comprising as component A a plasminogen activator and as component B hirudin together with a pharmaceutically acceptable carrier.

Suitable plasminogen activators are human t-PA and human u-PA in the two-chain or, preferably, one-chain form including glycosylated, partially glycosylated or unglycosylated forms obtained from natural sources or via recombinant DNA techniques from transformed mammalian cells or transformed microorganisms, such as *Escherichia coli* or *Saccharomyces cerevisiae*. Examples of such plasminogen activators are those described by M. Winkler et al. in Biochemistry 25, 4041–4045 (1986);

B. Rotzkin et al., Proc. Natl. Acad. Sci. USA 78, 3313-3317 (1981); D. Pennica et al., Nature 301, 214-221 (1983); and in European Patent Applications No. 41,766, 92,182, 93,619 and 143,081.

The term "plasminogen activator" includes furthermore mutants of human u-PA and human t-PA, u-PA/t-PA hybrid plasminogen activators and mutants of the latter, especially single-chain mutants and hybrids, furthermore fragments thereof retaining the fibrinolytic activity.

Mutants are especially those mutants which render the PA protease resistant. Such mutants are covalently modified at sites of proteolysis by proteases occuring in blood such as thrombin or plasmin, so that they are no longer susceptible to protease hydrolysis at these locations. The target sites of u-PA include $Lys^{135}$ to $Lys^{136}$ (cleavage at this site generates the so-called low molecular weight form of scu-PA or "LUK"), $Arg^{156}$ to $Phe^{157}$ (susceptible to thrombin attack) and $Lys^{158}$ to $Ile^{159}$ (cleavage at this site by plasmin generates tcu-PA). Suitable u-PA mutants have site specific substitutions, insertions or deletions of amino acid residues at one or more these target sites. Especially preferred are those mutants in which one amino acid residue or both amino acid residues forming the target sites are deleted or in which at least one of these amino acid residues is replaced by another amino acid residue so that the resulting mutants are resistant to proteolytic attack. For reference, see European Patent Applications No. 200,451, 210,279 and 288,435.

In further mutants of u-PA the unique N-glycosylation site occurring at $Asn^{302}$ ($Asn^{302}$-Ser-Thr) is modified such that glycosylation cannot take place at this site.

Scu-PA and preferred scu-PA mutants have the formula I cally glycosylated, or is another amino acid residue, and $Z_2$ is Thr or another amino acid residue different from Ser.

The term "amino acid residue" is intended to embrace the residues of all genetically encoded amino acids, such as acidic amino acid residues, for example the residues of glutamic acid and aspartic acid, basic amino acid residues, for example the residues of arginine, lysine and histidine, and neutral amino acid residues, for example the residues of asparagine, glutamine, methionine, glycine, alanine, leucine, isoleucine, valine, serine, threonine, phenylalanine, tyrosine or proline.

In order to prevent glycosylation at the N-glycosylation site the tripeptide sequences recognised as signal for N-glycosylation —Asn-L-Thr(or Ser)— wherein Asn is the acceptor and L can be any of the 20 genetically encoded amino acids except proline or aspartic acid which impede glycosylation has to be altered. Replacement of the Asn ($Z_1$) and/or Thr ($Z_2$) residues in the above tripeptide sequence by any other amino acid would abolish formation of glycosidic linkages at this site. For convenience, modification of the N-glycosylation site is not done at the protein level. Instead, it is advantageous to modify the gene coding for scu-PA in such a way that upon expression of said modified gene by a host a mutant scu-PA is produced in which the N-glycosylation site is altered in such a way that glycosylation cannot take place at this site. For replacement those amino acids are preferred which have a similar size and polarity as the amino acids to be replaced. The number of possible substituents is limited by the given nucleotide sequence in the corresponding DNA and the possible codons. Especially, asparagine is replaced by valine, leucine, isoleucine, alanine, serine, threonine or, in particular, glutamine, and threonine by valine, methionine or, in particular, alanine. For reference, see European Patent Application No. 288,435.

Preferred scu-PA compounds of the formula I are those in which $X_1$ is Lys, Gly or Ser, $X_2$ represents Lys, $Y_1$ is Arg, $Y_2$ is Phe, Asp or Glu, $Y_3$ is Lys, $Z_1$ is Asn or Gln and $Z_2$ is Thr.

| | | | | | | | | | | | | | | | (I) |
|---|---|---|---|---|---|---|---|---|---|---|---|---|---|---|---|
| Pro | Ser | Asn | Cys | Asp | Cys | Leu | Asn | Ser | Asn | Glu | Leu | His | Gln | Val | |
| Lys | Tyr | Phe | Ser | Asn | Ile | His | Trp | Gly | Gly | Thr | Cys | Val | Ser | Asn | |
| Gly | Gly | Gln | His | Cys | Glu | Ile | Asp | Cys | Asn | Cys | Pro | Lys | Lys | Phe | |
| Gly | Asn | Gly | His | Phe | Tyr | Arg | Gly | Lys | Ser | Lys | Thr | Cys | Tyr | Glu | |
| Gly | Arg | Pro | Cys | Leu | Pro | Trp | Asn | Lys | Ala | Ser | Thr | Asp | Thr | Met | |
| Thr | Tyr | His | Ala | His | Arg | Ser | Asp | Ser | Ala | Thr | Val | Leu | Gln | Gln | |
| Lys | His | Asn | Tyr | Cys | Arg | Asn | Pro | Ala | Leu | Gln | Leu | Gly | Leu | Gly | |
| Cys | Tyr | Val | Gln | Val | Gly | Leu | Lys | Asp | Asn | Arg | Arg | Arg | Pro | Trp | |
| Val | His | Asp | Cys | Ala | Asp | Gly | $X_1$ | Pro | Leu | Val | Gln | Glu | Cys | Met | |
| Glu | Leu | Lys | Phe | Gln | Cys | Gly | Gln | $X_2$ | Pro | Ser | Ser | Pro | Pro | Glu | |
| $Y_3$ | Ile | Ile | Gly | Gly | Glu | Phe | Thr | Lys | Thr | Leu | Arg | Pro | $Y_1$ | $Y_2$ | |
| Phe | Ala | Ala | Ile | Tyr | Arg | Arg | His | Thr | Ile | Glu | Asn | Gln | Pro | Trp | |
| Val | Cys | Gly | Gly | Ser | Leu | Ile | Ser | Arg | Gly | Gly | Ser | Val | Thr | Tyr | |
| Thr | His | Cys | Phe | Ile | Asp | Tyr | Pro | Pro | Cys | Trp | Val | Ile | Ser | Ala | |
| Tyr | Leu | Gly | Arg | Ser | Arg | Leu | Asn | Lys | Lys | Glu | Asp | Tyr | Ile | Val | |
| Lys | Phe | Glu | Val | Glu | Asn | Leu | Ile | Ser | Asn | Thr | Gln | Gly | Glu | Met | |
| Asp | Thr | Leu | Ala | His | His | Asn | Asp | Leu | His | Lys | Asp | Tyr | Ser | Ala | |
| Ser | Lys | Glu | Gly | Arg | Cys | Ala | Gln | Ile | Ala | Leu | Leu | Lys | Ile | Arg | |
| Ile | Cys | Leu | Pro | Ser | Met | Tyr | Asn | Pro | Ser | Arg | Thr | Ile | Gln | Thr | |
| Cys | Glu | Ile | Thr | Gly | Phe | Gly | Lys | Asp | Pro | Gln | Phe | Gly | Thr | Ser | |
| Tyr | Pro | Glu | Gln | Leu | Lys | Met | Thr | Glu | $Z_1$ | Ser | $Z_2$ | Asp | Tyr | Leu | |
| Arg | Glu | Cys | Gln | Gln | Pro | His | Tyr | Val | Val | Lys | Leu | Ile | Ser | His | |
| Lys | Met | Leu | Cys | Ala | Ala | Asp | Pro | Tyr | Gly | Ser | Glu | Val | Thr | Thr | |
| Gln | Gly | Asp | Ser | Gly | Gly | Pro | Leu | Gln | Trp | Lys | Thr | Asp | Ser | Cys | |
| Met | Thr | Leu | Thr | Gly | Ile | Val | Ser | Val | Gly | Arg | Leu | Gln | Gly | Arg | |
| Lys | Asp | Lys | Pro | Gly | Val | Tyr | Thr | Trp | Arg | Gly | Cys | Ala | Leu | Leu | |
| Trp | Ile | Arg | Ser | His | Thr | Lys | Glu | Val | Ser | His | Phe | Leu | Pro | | |
| | | | | | | | | Glu | Asn | Gly | Leu | Ala | Leu | | | in which $X_1$ and $X_2$ independently from each other represent Lys, an amino acid residue other than a basic amino acid residue or a chemical bond, $Y_1$ is Arg, an amino acid residue other than a basic amino acid residue or a chemical bond, $Y_2$ is Phe, an acidic amino acid residue or a chemical bond, $Y_3$ is Lys, an amino acid residue other than a basic amino acid residue or a chemical bond, $Z_1$ is Asn which is preferably yeast-specifi- Corresponding preferred scu-PA mutants are [Gly$^{135}$]-scu-PA, [Ser$^{135}$]-scu-PA, [Asp$^{157}$]-scu-PA, [Ser$^{135}$,Asp$^{157}$]-scu-PA and [Gly$^{135}$,Asp$^{157}$]-scu-PA wherein Asn$^{302}$ is yeast specifically glycosylated, and furthermore [Gln$^{302}$]-scu-PA, [Gly$^{135}$,Asp$^{157}$,Gln$^{302}$]-scu-PA and [Ser$^{135}$,Asp$^{157}$,Gln$^{302}$]-scu-PA.

The target site of t-PA with respect to proteolytic attack by proteases is in the sequence Phe$^{274}$-Arg$^{275}$-Ile$^{276}$-Lys$^{277}$. Suitable t-PA mutants have specific substitutions, insertions or deletions of amino acid residues at this site so that they are resistant to proteolytic attack (see above). For reference, see European Patent Applications No. 225,286, 227,462 and 233,013.

There are three sites for N-glycosidic linkage in the t-PA molecule: —Asn$^{117}$-Ser-Ser-, Asn$^{184}$-Gly-Ser- and Asn$^{448}$-Arg-Thr—.

T-PA and t-PA glycosylation mutants are, for example, those having the formula

| | | | | | | | | | | | | | | | | | (II) |
|---|---|---|---|---|---|---|---|---|---|---|---|---|---|---|---|---|---|
| Ser | Tyr | Gln | Val | Ile | Cys | Arg | Asp | Glu | Lys | Thr | Gln | Met | Ile | Tyr | Gln | Gln | |
| His | Gln | Ser | Trp | Leu | Arg | Pro | Val | Leu | Arg | Ser | Asn | Arg | Val | Glu | Tyr | Cys | |
| Trp | Cys | Asn | Ser | Gly | Arg | Ala | Gln | Cys | His | Ser | Val | Pro | Val | Lys | Ser | Cys | |
| Ser | Glu | Pro | Arg | Cys | Phe | Asn | Gly | Gly | Thr | Cys | Gln | Gln | Ala | Leu | Tyr | Phe | |
| Ser | Asp | Phe | Val | Cys | Gln | Cys | Pro | Glu | Gly | Phe | Ala | Gly | Lys | Cys | Cys | Glu | |
| Ile | Asp | Thr | Arg | Ala | Thr | Cys | Tyr | Glu | Asp | Gln | Gly | Ile | Ser | Tyr | Arg | Gly | |
| Thr | Trp | Ser | Thr | Ala | Glu | Ser | Gly | Ala | Glu | Cys | Thr | Asn | Trp | X$_1$ | Ser | Y$_1$ | |
| Ala | Leu | Ala | Gln | Lys | Pro | Tyr | Ser | Gly | Arg | Arg | Pro | Asp | Ala | Ile | Arg | Leu | |
| Gly | Leu | Gly | Asn | His | Asn | Tyr | Cys | Arg | Asn | Pro | Asp | Arg | Asp | Ser | Lys | Pro | |
| Trp | Cys | Tyr | Val | Phe | Lys | Ala | Gly | Lys | Tyr | Ser | Ser | Glu | Phe | Cys | Ser | Thr | |
| Pro | Ala | Cys | Ser | Glu | Gly | Asn | Ser | Asp | Cys | Tyr | Phe | Gly | X$_2$ | Gly | Y$_2$ | Ala | |
| Tyr | Arg | Gly | Thr | His | Ser | Leu | Thr | Glu | Ser | Gly | Ala | Ser | Cys | Leu | Pro | Trp | |
| Asn | Ser | Met | Ile | Leu | Ile | Gly | Lys | Val | Tyr | Thr | Ala | Gln | Asn | Pro | Ser | Ala | |
| Gln | Ala | Leu | Gly | Leu | Gly | Lys | His | Asn | Tyr | Cys | Arg | Asn | Pro | Asp | Gly | Asp | |
| Ala | Lys | Pro | Trp | Cys | His | Val | Leu | Lys | Asn | Arg | Arg | Leu | Thr | Trp | Glu | Tyr | |
| Cys | Asp | Val | Pro | Ser | Cys | Ser | Thr | Cys | Gly | Leu | Arg | Gln | Tyr | Ser | Gln | Pro | |
| Gln | Phe | Arg | Ile | Lys | Gly | Gly | Leu | Phe | Ala | Asp | Ile | Ala | Ser | His | Pro | Trp | |
| Gln | Ala | Ala | Ile | Phe | Ala | Lys | His | Arg | Arg | Ser | Pro | Gly | Glu | Arg | Phe | Leu | |
| Cys | Gly | Gly | Ile | Leu | Ile | Ser | Ser | Cys | Trp | Ile | Leu | Ser | Ala | Ala | His | Cys | |
| Phe | Gln | Glu | Arg | Phe | Pro | Pro | His | Leu | Thr | Val | Ile | Leu | Gly | Arg | Thr | | |
| Tyr | Arg | Val | Val | Pro | Gly | Glu | Glu | Glu | Gln | Lys | Phe | Glu | Val | Glu | Lys | Tyr | |
| Ile | Val | His | Lys | Glu | Phe | Asp | Asp | Asp | Thr | Tyr | Asp | Asn | Asp | Ile | Ala | Leu | |
| Leu | Gln | Leu | Lys | Ser | Asp | Ser | Ser | Arg | Cys | Ala | Gln | Glu | Ser | Ser | Val | Val | |
| Arg | Thr | Val | Cys | Leu | Pro | Pro | Ala | Asp | Leu | Gln | Leu | Pro | Asp | Trp | Thr | Glu | |
| Cys | Glu | Leu | Ser | Gly | Tyr | Gly | Lys | His | Glu | Ala | Leu | Ser | Pro | Phe | Tyr | Ser | |
| Glu | Arg | Leu | Lys | Glu | Ala | His | Val | Arg | Leu | Tyr | Pro | Ser | Ser | Arg | Cys | Thr | |
| Ser | Gln | His | Leu | Leu | X$_3$ | Arg | Y$_3$ | Val | Thr | Asp | 'Asn | Met | Leu | Cys | Ala | Gly | |
| Asp | Thr | Arg | Ser | Gly | Gly | Pro | Gln | Ala | Asn | Leu | His | Asp | Ala | Cys | Gln | Gly | |
| Asp | Ser | Gly | Gly | Pro | Leu | Val | Cys | Leu | Asn | Asp | Gly | Arg | Met | Thr | Leu | Val | |
| Gly | Ile | Ile | Ser | Trp | Gly | Leu | Gly | Cys | Gly | Gln | Lys | Asp | Val | Pro | Gly | Val | |
| Tyr | Thr | Lys | Val | Thr | Asn | Tyr | Leu | Asp | Trp | Ile | Arg | Asp | Asn | Met | Arg | Pro | | in which X$_1$, X$_2$ and X$_3$ each represent Asn or another genetically encoded amino acid, Y$_1$ and Y$_2$ each represent Ser or another genetically encoded amino acid other than Thr and Y$_3$ represents Thr or another genetically encoded amino acid other than Ser.

More particularly, the t-PA proteins have the formula II in which X$_1$, X$_2$ and X$_3$ each represent Asn and Y$_1$, Y$_2$ and Y$_3$ have the meanings given above.

Genetically encoded amino acids are those specified above.

For replacement of Asn in position X$_1$, X$_2$ and/or X$_3$ amino acids Gln, Thr and Ser are preferred. For replacement of Ser Y$_1$ and/or Y$_2$ and for the replacement of Thr Y$_3$ amino acids Ala and Asn are preferred.

Especially, only one of the radicals X$_1$ and Y$_1$ and/or only one of the radicals X$_2$ and Y$_2$ and/or only one of the radicals X$_3$ and Y$_3$ is replaced by another amino acid.

In particular, the t-PA mutants have the formula II in which one, two or three of the radicals X$_1$, X$_2$ and X$_3$ represent Asn and the other(s) represent(s) an amino acid residue selected from Gln, Thr and Ser, Y$_1$ and Y$_2$ each represent Ser and Y$_3$ represents Thr, or in which X$_1$, X$_2$ and X$_3$ each represent Asn, one or two of the radicals Y$_1$ and Y$_2$ represent Ser and the other(s) is (are) selected from the group consisting of Ala and Asn and Y$_3$ represents Thr, or in which X$_1$, X$_2$ and X$_3$ each represent Asn, Y$_1$ and Y$_2$ each represent Ser and Y$_3$ is selected from the group consisting of Ala and Asn.

Especially, the t-PA mutants have the formula II in which X$_1$, X$_2$ and X$_3$ each represent Asn, and at least one of radicals Y$_1$, Y$_2$ and Y$_3$ is Ala or Asn and the other(s) is (are) Ser (Y$_1$ and Y$_2$) or Thr (Y$_3$).

Examples of such t-PA mutants are [Asn$^{119}$]-t-PA, [Ala$^{186}$]-t-PA, [Ala$^{450}$]-t-PA, [Asn$^{119}$, Ala$^{186}$]-t-PA, [Asn$^{119}$, Ala$^{186}$, Asn$^{450}$]-t-PA and [Asn$^{119}$, Ala$^{186}$, Ala$^{450}$]-t-PA.

Fragments of u-PA and t-PA are especially those in which segments or domains of natural u-PA or t-PA which are not essential for fibrinolytic activity are deleted. Such fragments and processes for their preparation are known per se.

U-PA/t-PA hybrid plasminogen activators are especially single-chain hybrid PAs comprising an amino acid sequence containing all or discrete A-chain domains of human u-PA or discrete A-chain domains of human u-PA and human t-PA, linked in series to the catalytic region of human t-PA and single-chain hybrid PAs comprising an amino acid sequence containing all or discrete A-chain domains of human t-PA or discrete A-chain domains of human t-PA and u-PA, linked in series to the catalytic region of human u-PA as disclosed in European Patent Application No. 277,313 or a single-chain hybrid PA differing from u-PA in that the amino acid segment following the u-PA kringle up to the u-PA activation site is replaced by the amino acid segment following the t-PA kringle 2 up to the t-PA activation site.

Preferred hybrid PAs contain the catalytic region of human u-PA.

In particular, the single-chain hybrid PAs comprise an amino acid sequence selected from the group consisting of an amino acid sequence containing all of the A-chain domains of human t-PA, an amino acid sequence containing discrete A-chain domains of human t-PA, such as the finger domain or a kringle, especially the kringle 2, domain of human t-PA, and an amino acid sequence containing two, three or four A-chain domains of human t-PA and/or human u-PA, especially two or three domains of human t-PA or two or three domains of human u-PA and human t-PA, such as the finger, growth factor and kringle 2 domains of human t-PA, the finger and kringle 2 domains of human t-PA or the u-PA growth factor and t-PA kringle 2 domains, which amino acid sequence is linked in series to the catalytic region of human u-PA, and an amino acid sequence containing the u-PA growth factor and t-PA kringle 2 domains which amino acid sequence is linked in series to the catalytic region of human t-PA.

Preferably, the hybrid PA amino acid sequence starts with the N-terminal amino acids 1 to 5 of t-PA or the N-terminal amino acids 1 to 12 of u-PA or starts with any junction sequence naturally N-terminally linked to the first domain of the hybrid PA or with a fragment of such a junction sequence which fragment preferably has at least five amino acid residues.

In the hybrid PAs the A-chain domains are connected via natural junction sequences, fused junction sequences or hybrid junction sequences or fragments thereof. Thus, a first domain is linked to a second domain by the junction sequence naturally occurring at the C-terminus of the first domain, by the junction sequence naturally occurring at the N-terminus of the second domain, by a fused junction sequence composed of said junction sequences or by fragments thereof.

The A-chain domains of the hybrid PAs according to the invention are linked to the B-chain serine protease region by a junction sequence selected from the group consisting of the junction sequence linking the kringle 2 domain to the B-chain in human t-PA, the junction sequence linking the kringle domain to the B-chain in human u-PA and a hybrid sequence composed of subsequences of said junction sequences wherein said junction sequence includes a processing site capable of being cleaved by plasmin and, N-terminally thereto, a cysteine residue which can participate in a sulphur-sulphur bridge to the catalytic B-chain region, the junction sequence preferably having at least fourty and up to 60 amino acid residues.

Most preferred is the junction of the domains at a position which is defined by the exon-intron junctions on the corresponding DNA. The junction of the A-chain to the B-chain is most preferably at the activation site.

In particular, the single chain hybrid plasminogen activators are selected from the group consisting of such a hybrid plasminogen activator comprising the A-chain of u-PA or an A-chain essentially consisting of the u-PA growth factor and the t-PA kringle 2 domains linked in series to the catalytic region (B-chain) of t-PA, and a hybrid plasminogen activator comprising the A-chain of t-PA, an A-chain essentially consisting of the finger domain of t-PA, and A-chain essentially consisting of the u-PA growth factor and t-PA kringle 2 domains, an A-chain essentially consisting of the t-PA finger and kringle 2 domains or an A-chain essentially consisting of the t-PA finger, growth factor and kringle 2 domains said A-chain being linked in series to the catalytic region (B-chain) of u-PA, wherein the A-chain is linked to the B-chain via a junction sequence comprising an activation site and a cysteine residue capable of forming a sulphur-sulphur bond to the B-chain or the single chain hybrid plasminogen activator comprises an A-chain essentially consisting of the t-PA kringle 2 domain linked to the catalytic region (B-chain) of u-PA at the activation site.

Especially preferred is a single chain hybrid plasminogen activator selected from the group consisting of such a hybrid PA comprising an A-chain essentially consisting of the u-PA growth factor domain and the t-PA kringle 2 domain linked in series to the catalytic region (B-chain) of t-PA, and a hybrid PA comprising an A-chain essentially consisting of the t-PA kringle 2 domain or of the t-PA finger and kringle 2 domains linked in series to the catalytic region (B-chain) of u-PA, wherein the junction between the A-chain domains(s) and the B-chain is at the activation site.

Preferred hybrid PAs according to the invention are
[uPA(1-158)-tPA(276-527)],
[uPA(1-131)-tPA(263-527)],
[tPA(1-275)-uPA(159-411)],
[tPA(1-262)-uPA(132-411)],
[uPA(1-44)-tPA(176-261)-uPA(134-411)],
[tPA(1-49)-tPA(262-275)-uPA(159-411)],
[tPA(1-49)-uPA(134-411)],
[tPA(1-49)-tPA(176-275)-uPA(159-411)],
[tPA(1-49)-tPA(176-262)-uPA(132-411)],
[uPA(1-44)-tPA(176-527)],
[uPA(1-44)-tPA(176-275)-uPA(159-411)],
[uPA(1-133)-tPA(262-275)-uPA(159-411)],
[tPA(1-3)-tPA(176-275)-uPA(159-411)],
[tPA(1-86)-tPA(176-275)-uPA(159-411)] and
[tPA(1-86)-tPA(176-262)-uPA(132-411)].

Especially preferred are hybrid plasminogen activators [uPA(1-44)-tPA(176-527)], [tPA(1-49)-tPA(176-275)-uPA(159-411)] and [tPA(1-3)-tPA(176-275)-uPA(159-411)].

In the mutants of the hybrid PAs at least one, preferably all, of the N-glycosylation sites are modified such that glycosylation cannot take place at this (these) site(s).

Especially, asparagine is replaced by valine, leucine, isoleucine, alanine or, in particular, glutamine, and serine or threonine by valine, methionine or, in particular, alanine.

Preferred modified hybrid PAs are
[tPA(1-49)-tPA(262-275)-uPA(159-301, Gln, 303-411)],
[tPA(1-49)-tPA(176-185, Ala, 187-275)-uPA(159-301, Gln, 303-411)],
[uPA(1-44)-tPA(176-185, Ala, 187-449, Ala, 451-527)],
[tPA(1-3)-tPA(176-185, Ala, 187-275)-uPA(159-301, Gln, 303-411)],
[tPA(1-86)-tPA(176-185, Ala, 187-275)-uPA(159-301, Gln, 303-411)],
[tPA(1-49)-tPA(176-275)-uPA(159-301, Gln, 303-411)],
[tPA(1-3)-tPA(176-275)-uPA(159-301, Gln, 303-411)],
[uPA(1-44)-tPA(176-449, Ala, 451-527)],
[tPA(1-86)-tPA(176-275)-uPA(159-301, Gln, 303-411)],
[uPA(1-133)-tPA(262-275)-uPA(159-301, Gln, 303-411)],
[uPA(1-133)-tPA(262-275)-uPA(159-303, Asn, 305-411)],
[uPA(144)-tPA(176-185, Ala, 187-275)-uPA(159-301, Gln, 303-411)] and
[uPA(1-44)-tPA(176-185, Ala, 187-275)-uPA(159-303, Asn, 305-411)].

The term "hirudin" includes hirudins obtained from natural sources, such as from the leech Hirudo medicinalis, hirudins obtained via recombinant DNA techniques, as well as mutants and fragments thereof retaining the unique thrombin inhibitory activity. A number of such hirudins have been published by D. Tripier [Folia Haematol. 115, 30 (1988)].

The hirudin component of the compositions according to the invention is, for example, hirudin variant HV1 [D. Bagdy et al., Methods Enzymol. 45, 669–678 (1976); U.S. Pat. No. 4,745,177] having the formula

| Val | Val | Tyr | Thr | Asp | Cys | Thr | Glu | Ser | Gly | (III) |
|-----|-----|-----|-----|-----|-----|-----|-----|-----|-----|-------|
| Gln | Asn | Leu | Cys | Leu | Cys | Glu | Gly | Ser | Asn | |
| Val | Cys | Gly | Gln | Gly | Asn | Lys | Cys | Ile | Leu | |
| Gly | Ser | Asp | Gly | Glu | Lys | Asn | Gln | Cys | Val | |
| Thr | Gly | Glu | Gly | Thr | Pro | Lys | Pro | Gln | Ser | |
| His | Asn | Asp | Gly | Asp | Phe | Glu | Glu | Ile | Pro | |
|     |     | W   |     |     |     |     |     |     |     | |
|     |     | \|  |     |     |     |     |     |     |     | |
| Glu | Glu | Tyr | Leu | Gln |     |     |     |     |     | | wherein W represents the phenolic hydroxy group of Tyr (desulfato hirudin HV1) or a group of the formula $-O-SO_3H$ (hirudin HV1), hirudin variant HV2 [cf. R. P. Harvey et al., Proc. Natl. Acad. Sci. USA 83, 1084–1088 (1986)] having the formula

| Ile | Thr | Tyr | Thr | Asp | Cys | Thr | Glu | Ser | Gly | Gln | Asn | Leu | Cys | (IV) |
|-----|-----|-----|-----|-----|-----|-----|-----|-----|-----|-----|-----|-----|-----|------|
| Leu | Cys | Glu | Gly | Ser | Asn | Val | Cys | Gly | Lys | Gly | Asn | Lys | Cys | |
| Ile | Leu | Gly | Ser | Asn | Gly | Lys | Gly | Asn | Gln | Cys | Val | Thr | Gly | |
| Glu | Gly | Thr | Pro | Asn | Pro | Glu | Ser | His | Asn | Asn | Gly | Asp | Phe | |
| Glu | Glu | Ile | Pro | Glu | Glu | Tyr | Leu | Gln |     |     |     |     |     | | and hirudin variant PA [cf. J. Dodt et al., Biol. Chem. Hoppe-Seyler 367, 803–811 (1986)] having the formula

| Ile | Thr | Tyr | Thr | Asp | Cys | Thr | Glu | Ser | Gly | Gln | Asn | Leu | Cys | (V) |
|-----|-----|-----|-----|-----|-----|-----|-----|-----|-----|-----|-----|-----|-----|-----|
| Leu | Cys | Glu | Gly | Ser | Asn | Val | Cys | Gly | Lys | Gly | Asn | Lys | Cys | |
| Ile | Leu | Gly | Ser | Gln | Gly | Lys | Asp | Asn | Gln | Cys | Val | Thr | Gly | |
| Glu | Gly | Thr | Pro | Lys | Pro | Gln | Ser | His | Asn | Gln | Gly | Asp | Phe | |
| Glu | Pro | Ile | Pro | Glu | Asp | Ala | Tyr | Asp | Glu |     |     |     |     | | or a fragment or a mutant of any of said hirudin variants.

Especially preferred is desulfato hirudin HV1.

Suitable fragments of such hirudin variants, especially of hirudin variant HV1, are known, for example from FEBS Lett. 211, 10 (1987), J. Med. Chem. 31, 1009 (1988), Biochemistry 27, 8170 (1988), J. Biol. Chem. 264, 8692 (1989) and from EP 276014, and consist, for example, of the 9 to 30 C-terminal amino acids of hirudin HV1 or PA. Further fragments include, for example, hirudin HV1 lacking the C-terminal amino acid Gln or the C-terminal dipeptide residue Leu-Gln.

Mutants of the hirudin according to the invention include hirudins, especially hirudin HV1, carrying site specific mutations at the N-terminus, in the core region or at the C-terminus. Such N-terminal mutants of hirudin HV1 are, for example, [Ile$^{1,2}$]-desulfato hirudin HV1 (in which the N-terminal amino acids Val-Val are replaced by Ile-Ile) or [Gly$^1$]-desulfato hirudin HV1 (in which the N-terminal amino acid Val is replaced by Gly). Corresponding C-terminal mutants of hirudin HV1 include, for example, [Gln$^{57,58,61,62}$]-desulfato hirudin HV1 (in which amino acids 57, 58, 61 and 62 have been replaced by Gln) and [Pro$^{66}$]-desulfato hirudin HV1 (carrying an additional Pro residue at the C-terminus). Corresponding core mutants of desulfato hirudin HV1 include, for example, [Gln$^{27}$, Arg$^{47}$]-desulfato hirudin HV1 which additionally may carry an extra Met residue at the N-terminus ([Met$^0$,Gln$^{27}$,Arg$^{47}$]-desulfato hirudin HV1) and [Gln$^{27}$,Gln$^{36}$,Arg$^{47}$]-desulfato hirudin HV1. A further mutant is [des-Val$^1$,Thr$^2$]-desulfato hirudin HV1. A mutant of hirudin HV2 is, for example, [Lys$^{47}$]-hirudin HV2. All of these mutants are known or can be prepared by methods known in the art, for example by subjecting the gene coding for the respective parent hirudin to site-specific mutagenesis and expressing the mutated hirudin gene in a suitable host such as yeast.

Further mutants of said hirudins are, for example, those disclosed in European Patent Application No. 273,800.

In particular, the invention concerns a pharmaceutical composition comprising as component A a plasminogen activator selected from the group consisting of
(1) scu-PA,
(2) t-PA,
(3) a sct-PA mutant of the formula II in which $X_1$, $X_2$ and $X_3$ each represent Asn, and at least one of radicals $Y_1$, $Y_2$ and $Y_3$ is Ala or Asn and the other(s) is (are) Ser ($Y_1$ and $Y_2$) or Thr ($Y_3$), and
(4) a single chain u-PA/t-PA hybrid plasminogen activator selected from such a hybrid PA comprising an A-chain essentially consisting of the u-PA growth factor domain and the t-PA kringle 2 domain linked in series to the catalytic region (B-chain) of t-PA, and a hybrid PA comprising an A-chain essentially consisting of the t-PA kringle 2 domain or of the t-PA finger and kringle 2 domains linked in series to the catalytic region (B-chain) of u-PA, wherein the junction between the A-chain domain(s) and the B-chain is at the activation site, and as component B desulfato hirudin HV1, together with a pharmaceutically acceptable carrier.

In most preferred pharmaceutical compositions according to the invention the component A is selected from the group consisting of scu-PA, t-PA, [Ala450]-t-PA, [Asn119, Ala186, Ala450]-t-PA, [uPA(1-44)-tPA(176-527)], [tPA(1-14 49)-tPA(176-14 275)-uPA(159-411)] and [tPA(1-14 3)-tPA(176-275)-uPA(159-411)], and component B is desulfato hirudin HV1.

The plasminogen activators and hirudins according to the invention are known compounds. Especially preferred are those PAs and hirudins which have been prepared by recombinant DNA techniques making use of transformed mammalian or yeast cells, as described, for example, in European Patent Applications No. 143,081, 225,286, 200,655, 225,633 and 277,313.

The novel combination compositions according to the invention can be used in mammals (humans or animals) for the prevention or treatment of thrombosis or diseases caused by thrombosis, arteriosclerosis, myocardial and cerebral infarction, venous thrombosis, thromboembolism, post-surgical thrombosis, thrombophlebitis, etc.

The pharmaceutical compositions according to the invention can be used for the treatment of the above-mentioned indications when they are administered parenterally, such as intravenously or, as regards hirudin, also subcutaneously.

There are suitable infusion or injection solutions, preferably aqueous isotonic solutions or suspensions, it being possible to prepare these before use, for example from lyophilised preparations that contain the active ingredient(s) alone or together with a pharmaceutically acceptable carrier, such as mannitol, lactose, dextrose, human serum albumin and the like. The pharmaceutical compositions are sterilized and, if desired, mixed with adjuncts, for example preservatives, stabilisers, emulsifiers, solubilisers, buffers and/or salts (such as 0.9% sodium chloride) for adjusting the isotonicity. Sterilization can be achieved by sterile filtration through filters of small pore size (0.45 μm diameter or smaller) after which the composition can be lyophilised, if desired. Antibiotics may also be added in order to assist in preserving sterility. For example, standard formulation techniques developed for the administration of PAs (i.e. European Patent Applications No. 93,619, 41,766, 112,940 and others) or novel compositions confering sufficient solubility to the PA in low pH buffered media (examples are in European Patent Application No. 211,592, German Offenlegungsschrift No. 3,617,752, 3,617,753, 3,642,960) may be used. Hirudins are as such highly soluble in aqueous solutions and need no additives for enhanced solubility. For stability reasons it is recommended to reconstitute lyophylized samples in 5% dextrose or 5% mannitol or 0.9% sodium chloride and the like.

The combination compositions according to the invention are in a state to allow the active ingredients (plasminogen activator and hirudin) to be administered (e.g. infused) at the same time and by the same route (i.e. cannula) or to apply first hirudin, preferably by bolus injection, and then, starting within 5 to 10 minutes thereafter, the second component, especially the plasminogen activator, preferably by infusion, or, in particular, to apply first the total dose of hirudin together with a small quantity, for example 5 to 20%, of the plasminogen activator by bolus injection and then, starting within 5 to 10 minutes thereafter, the main quantity of the plasminogen activator by infusion. Infusion is done within 30 minutes to 3 hours.

Depending upon the type of the disease and the age and the condition of the patient, the daily dose to be administered once for the treatment of a patient weighing approximately 70 kg is in the range from 10 to 200, especially 20 to 100 mg, plasminogen activator and 5 to 100 mg, especially 10 to 30 mg, hirudin [especially a dosis which leads to a times two prolongation of activated partial thromboplastin time (aPTT)]. Accordingly, the weight ratio between the plasminogen activator and the hirudin in the composition may vary, in general between 20:1 and 2:1. A weight ratio between 5:1 and 2:1 is preferably used.

The pharmaceutical compositions according to the present invention are dispensed in unit dosage forms, for example in ampoules comprising therapeutically effective amounts of both components (plasminogen activator and hirudin) or, preferably, in double ampoules comprising therapeutically effective amounts of the components separately, together with a pharmaceutically acceptable carrier.

The present pharmaceutical compositions are produced in a manner known per se applying conventional lyophilising or dissolving procedures, for example, if necessary, by mixing the plasminogen activator and the hirudin and optionally the pharmaceutically acceptable carrier, and, for the preparation of a lyophilisate, freeze-drying an aqueous solution obtained. The compositions contain from approximately 0.1% to 20%, especially from approximately 1% to 10%, and in the case of lyophilisates up to 100% of the active ingredients.

The invention relates also to the use of the combination compositions according to the invention for the prophylactic and therapeutic treatment of the human or animal body, especially for the above-mentioned clinical syndromes, in particular for the prophylaxis and therapy of thrombosis or diseases caused by thrombosis in the human or animal body.

A further object of the present invention is founded on the surprising observation that hirudin is a powerful agent which dramatically reduces the reocclusion (new formation of thrombi) rate of vessels (veins or arteries) which have previously been opened by mechanical (PTCA) or chemical (lysis) means and thus improves the prospects of definitely curing the coagulation disorder. Accordingly, the invention concerns a method for preventing the reocclusion of previously occluded and mechanically or chemically reopened blood vessels in a mammal comprising administering to said mammal a therapeutically effective amount of hirudin. Preferably, the administration of hirudin follows immediately after the opening of the occluded vessels, for example after termination of the thrombolytic therapy using, for example, plasminogen activators optionally in combination with antithrombotic agents. Depending upon the type of the disease and the age and the condition of the patient, the daily dose of hirudin to be administered by infusion or, preferably, by two bolus injections, for the treatment of a patient weighing approximately 70 kg is in the range from 20 to 100 mg, especially about 50 to 70 mg. The anti-reocclusion therapy using hirudin is continued until the risk of reocclusion has minimized, for example for about 1 to 3 weeks, in particular for about 2 weeks.

BRIEF DESCRIPTION OF THE DRAWINGS

In the following experimental part various embodiments of the present invention are described with reference to the accompanying drawings in which:

FIG. 3 schematically illustrates the construction of plasmid pML350.

FIG. 4 schematically shows the plasmid map of plasmid pJDB207/GAPFL-HIR.

Figure 1:
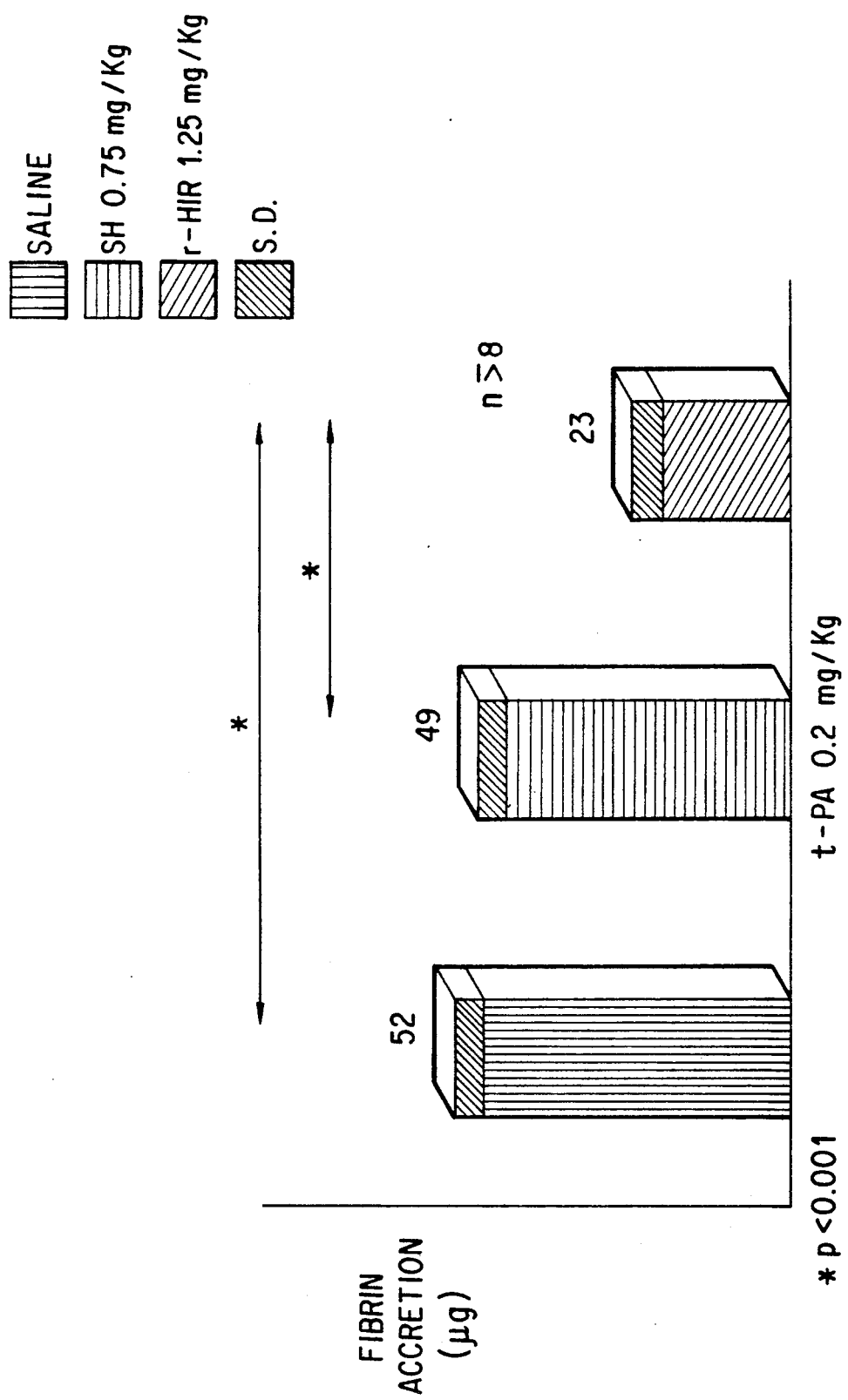
FIG. 1 shows the fibrin accretion during dissolution of the clot by t-PA in the presence of heparin and desulfato hirudin, respectively.

The following Examples illustrate the invention without implying any limitation.

EXAMPLE 1

In Vitro Clot Lysis

Human blood is directly withdrawn into 3.8% sodium citrate solution (ratio blood/citrate solution 9:1). The mixture is centrifuged at 1,000 rpm for 10 min to yield citrated plasma.

A mixture consisting of 150 μl citrated plasma 125 μl 0.9% sodium chloride solution 100 μl desulfato hirudin HV1 or MCI-9038 (see below) in 0.9% sodium chloride is prepared directly in 1 ml cuvettes equilibrated at 37° C. The mixture is incubated for 15 min at 37° C. Then, 25 μl of a 1 μg/ml t-PA stock solution (American Diagnostica, New York) and 300 μl 0.0025M calcium chloride solution are added to start coagulation.

The change in the optical density (coagulation) is continuously measured at 608 nm in a Uvikon 810 P spectrophotometer equipped with a kinetic program.

The time (in minutes) from addition of the $CaCl_2$ solution to a change in absorbance greater than 0.025 is defined as the coagulation time. The clot lysis time (in minutes) is defined as the time from the beginning of the clotting to the time at which the absorbance decreased to 10% of the maximum absorbance.

The thrombin inhibitor MCI-9038 [(2R,4R)-4-methyl-1-[$N^2$-[(3-methyl-1,2,3,4-tetrahydro-8-quinolyl)-sulfonyl]-L-arginyl]-2-piperidinecarboxylic acid] is chemically synthesized as described in S. Okamoto et al., Biochem. Biophys. Res. Commun. 101, 440-446 (1981). It is used at the following end concentrations: 0.07, 0.14, 0.28, 0.56 and 1.1 μM. The desulfato hirudin used has been prepared by recombinant DNA technology using transformed yeast according to the procedure described in European Patent Application No. 225,633. It is used at the following end concentrations: 0.8, 1.6, 3.2, 8 and 16 nM. The concentrations chosen of MCI-9038 and desulfato hirudin are equipotent concentrations in terms of prolongation of clotting time (coagulation), e.g. 1.2 μM MCI-9038 and 16 nM desulfato hirudin lead to the same prolongation of aPTT.

It is evident that in order to achieve the same effect as exhibited by a given concentration in desulfato hirudin, the twenty-fold concentration in MCI-9038 has to be taken.

EXAMPLE 2

Rabbit Jugular Vein Thrombosis Model

The experiments are performed with New Zealand white rabbits (weighing 2.3-3.5 kg) anaesthesized by intravenous (marginal ear vein) injection of 30 mg/kg sodium pentobarbital.

Through a paramedical incision of the neck, the jugular veins and the right carotid artery are exposed. The right carotid artery is cannulated with a 1.5 mm diameter polyethylene cannula for blood sampling. The two jugular veins are isolated, cleared over a distance of 2 cm, small side branches are ligated. Each jugular segment is emptied of blood and blood flow is temporarily occluded both proximally and distally by two angiostaths, 1.5 cm apart. A 10 cm length 3.0 TiCron braided polyester suture, presoaked in a collagen solution, is introduced lengthwise in the lumen of the isolated jugular vein for a distance of 4 cm to avoid the embolization of the thrombus to be produced. 150 μl of citrated rabbit blood containing 5 μl of $^{125}$I-fibrinogen (approx. 500 000 cpm) is then aspirated in a 1 ml tubercoline syringe containing 50 μl (5 I.U.) of thrombin and 10 μl of $CaCl_2$ (0.25M). The components are quickly mixed and injected into the isolated segment of the jugular vein via a 25 gauge needle. Thrombi are allowed to age for 30 min and then both vessel clamps are removed and blood flow restored.

a) Enhancement of t-PA induced lysis by desulfato hirudin HV1

Intravenous infusions are carried out by using a constant rate infusion pump. t-PA derived from melanoma cell cultures is obtained from BioResponse, USA. A total dose of 0.5 mg t-PA is infused through the marginal ear vein over a period of 3 hours. Along with t-PA either saline, standard heparin (KabiVitrum, Sweden, 140 USP/mg; 0.75 mg/kg) or hirudin (1 mg/kg) are infused. Doses of heparin and hirudin are used which give in control experiments the same prolongation in aPTT (activated partial thromboplastin time), e.g. times two.

As a control a group of animals is only infused with saline without addition of t-PA. At the end of the infusion, the thrombi remaining in the vessel are removed and their size is determined by measuring the amount of residual $^{125}$I-labeled fibrinogen remaining in the thrombi and comparing the results with those of the saline controls.

The results of the experiment are summarized in Table 1.

TABLE 1

| Combination | % lysis | Mean of n animals |
| --- | --- | --- |
| First set of experiments | | |
| t-PA + saline | 44 | n = 5 |
| t-PA + desulfato hirudin | 52 | n = 12 |
| Second set of experiments | | |
| t-PA + saline | 37 | n = 18 |
| t-PA + heparin | 34 | n = 18 | b) Inhibition of thrombus accretion by desulfato hirudin HV1 in t-PA treated rabbits The effects of standard heparin and recombinant desulfato hirudin in preventing thrombus extension during thrombolysis with t-PA are assessed as their ability to inhibit the accretion of $^{125}$I-fibrinogen onto autologous non-radioactive thrombi preformed in the jugular vein of rabbits. Standard sized non-radioactive thrombi are produced as described above. 15 min after the thrombi are formed each animal is injected with 10 μCi of $^{125}$I-fibrinogen. Five min later the infusion of t-PA along with standard heparin or desulfato hirudin is started (concentrations as in Example 2a). At the end of the three hours infusion, the venous segments containing the thrombi are tied off, split open longitudinally and the remaining thrombi are removed. The specific activity of the whole blood fibrinogen is estimated from the mean of the blood samples collected at hourly intervals throughout the infusion. The ratio of the radioactivity of the thrombus to the circulating fibrinogen radioactivity is used to quantify thrombus size, which is then expressed as μg or $^{125}$I-fibrinogen accreted onto the thrombus.

Figure 2:
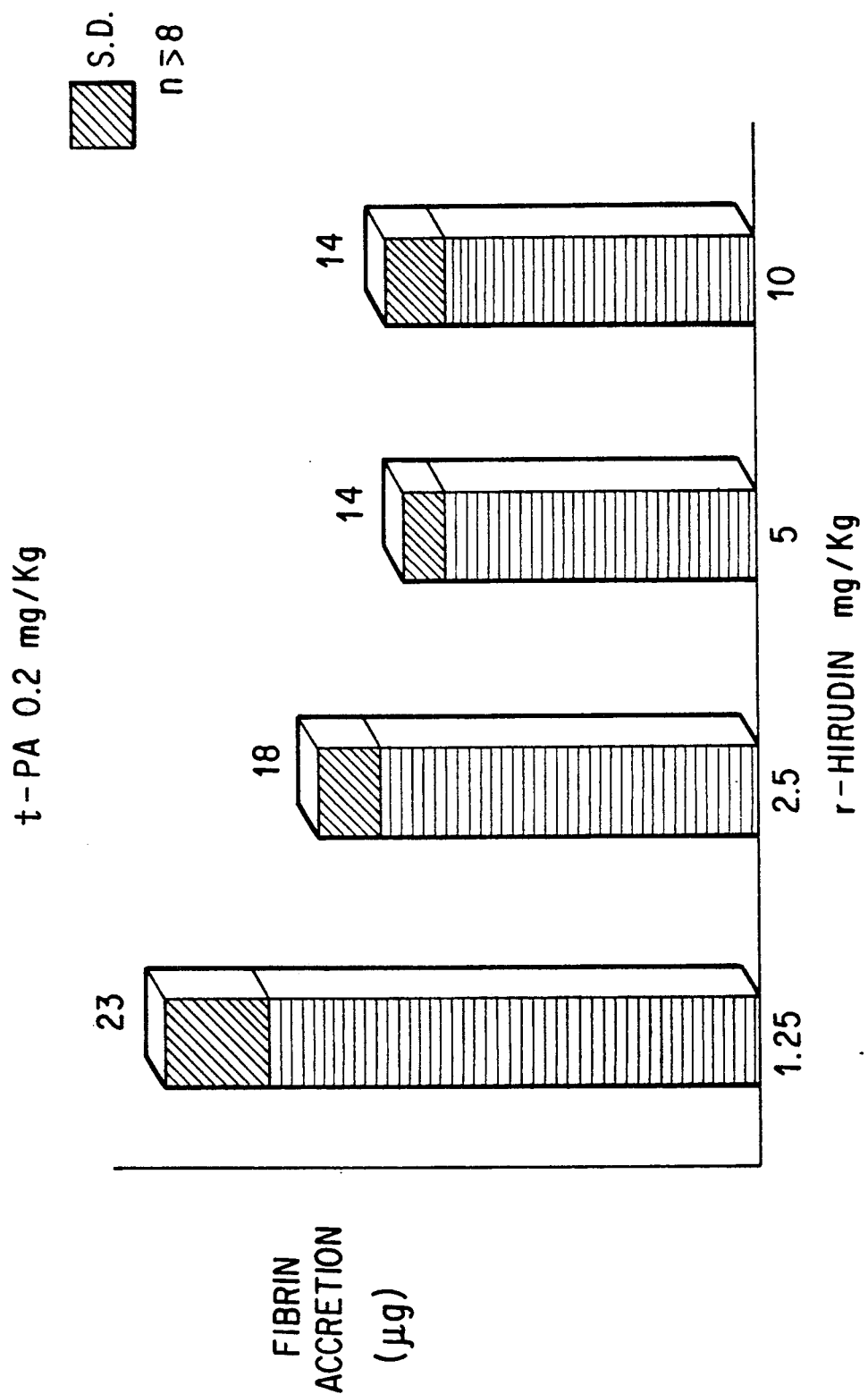
FIG. 2 shows the fibrin accretion during dissolution of the clot by t-PA in the presence of various concentrations of desulfato hirudin.

The results are summarized in FIG. 1 and FIG. 2.

FIG. 1 shows that even during the dissolution of the clot new $^{125}$I-fibrinogen—>fibrin is deposited on the surface of the preformed clot (e.g. 52 μg with only t-PA). Heparin has clearly no beneficial effect (49 versus 52 μg, statistically not significant), whereas desulfato hirudin shows a clear reduction in thrombus accretion (SH: standard heparin; S.D.: standard deviation; r-HIR: recombinant desulfato hirudin).

FIG. 2 shows that with increasing concentrations of desulfato hirudin this effect can even be potentiated.

The same effects are observed when a plasminogen activator different from t-PA, such as scu-PA or a u-PA/t-PA hybrid plasminogen activator, or another hirudin compound, such as desulfato hirudin PA or a hirudin mutant, is used in the combination treatment. Corresponding hirudin mutants can be prepared as described in Example 3.

EXAMPLE 3

Production of Desulfato Hirudin HV1 Mutants

A. Construction of the plasmid pML350 (see FIG. 3)

a) Digestion of the DNA of plasmid pIN-III-ompA-2

10 μg of plasmid pIN-III-ompA-2 [J. Ghrayeb et al., EMBO-J. 3, 2437 (1984)] are dissolved in 25 μl of 100 mM Tris-HCl pH 7.5, 50 mM NaCl and 100 μg/ml gelatine and are digested with the restriction endonucleases EcoRI and BamHI. The solution is adjusted to TNE and extracted with phenol/chloroform. The DNA is precipitated with ethanol. The vector DNA pIN-III-ompA-2/EcoRI/BamHI is isolated after electrophoresis in agarose by gel elution.

b) Digestion of the DNA of plasmid pML310

20 μg of the plasmid pML310 (see European Patent Application No. 168342) are digested in 50 μl of 100 mM Tris-HCl pH 7.5, 50 mM NaCl and 100 μg/ml gelatine with the restriction endonucleases EcoRI and BamHI. The solution is adjusted to TNE and extracted with phenol/chloroform. The DNA is precipitated with ethanol. The $F_1$-$F_2$-DNA (hirudin gene) is isolated after gel electrophoresis in agarose by gel elution.

c) Ligation of the $F_1$-$F_2$-DNA (hirudin gene) from pML310 with the vector DNA pIN-III-ompA-2/EcoRI/BamHI 1 μg of $F_1$-$F_2$-DNA (hirudin gene)/EcoRI/BamHI and 30 μg of the vector DNA pIN-III-ompA-2/EcoRI/BamHI are dissolved in 50 μl of 100 mM Tris-HCl pH 7.5, 50 mM NaCl and 100 μg/ml gelatine, adjusted to TNE. The solution is extracted with phenol/chloroform and the DNA is precipitated with ethanol. The DNA precipitate is dissolved in 20 μl of a solution of 50 mM Tris-HCl (pH 7.8), 10 mM $MgCl_2$, 10 mM DTT, 0.5 mM ATP, and 100 μg/l gelatine and treated with 25 units/μl $T_4$ DNA ligase (Biolabs) at 15° C. for 3 h. By this way the recombinant plasmid pML350 is created, which contains the $F_1$-$F_2$-DNA (hirudin gene) inserted.

d) Transformation of E. coli HB101 with plasmid pML350

The E. coli HB101 cells pretreated with calcium that are prepared as described by Mandel et al. [J. Mol. Biol. 53, 159 (1970)].

The solution obtained in c), which contains the recombinant plasmid pML350, is heated at 65° C. for 10 min in order to inactivate the $T_4$ DNA ligase and is then cooled to 37° C. 10 μl of the resulting reaction mixture are added to 150 μl of calcium-treated E. coli HB101 cells in 10 mM $MgCl_2$ and 10 mM Tris.HCl (pH 7.5) in a total volume of 200 μl.

Subsequently, this mixture is cooled in ice for 30 min, heated for 2 min at 42° C. and then left to stand for 50 min in 1 ml of L-medium (Bacto tryptone 10 g/l; Bacto yeast extract 5 g/l; NaCl 5 g/l; glucose 5 g/l; ampicillin 0.1 g/l) at 37° C. The mixture is then spread out in aliquots of 0.2 ml on 5 agar plates (McConkey Agar, Difco), which contain 60 μg/ml of ampicillin (Serva). The agar plates are then maintained at 37° C. for 16–18 hours. 185 ampicillin resistant colonies of transformed E. coli HB101 cells are obtained.

e) Screening the colonies that contain $F_1$-$F_2$-DNA 6 transformed colonies are pressed off onto nitrocellulose filter B85 (Schleicher and Schull). In accordance with Grunstein and Hogness [Proc. Natl. Acad. Sci. USA 72, 3961 (1979)] the colonies are lysed and their denatured DNA is fixed on the filter. Subsequently prehybridization of the filters is carried out in 20 ml (per filter) of 4×SET [=solution of 30 mM Tris•HCl (pH 8), 150 mM NaCl, 1 mM EDTA], 0.1% (w/v) Ficoll 400 (Pharmacia), 0.5% SDS, 50 μg/ml denatured calf thymus DNA for 4 h at 64° C. Subsequently the nitrocellulose filters are treated in 20 ml (per filter) of 5×SET (w/v), 0.1% (w/v) Ficoll 400, 0.2% SDS and 50 μl/ml denatured calf thymus DNA for 16 h at 64° C. with the $^{32}P$ radioactively labelled probe (approximately $10^3$–$10^4$ Cerencov cpm per filter). A mixture consisting of oligonucleotides 46/64 complementary, 1/58, 96/67 and 154/64 complementary (see European Patent Application No. 168342) is used as probe.

Subsequently, the filters are washed twice in 2×SET, 0.2% SDS at room temperature, then twice in 2×SET, 0.5% SDS at 60° C. (first for 30 min, then for 60 min). The filters are then dried between 3 MM paper (Whatman) and placed at −80° C. on an X-ray film (Fuji) with an intensifying screen (Ilford) for 1–2 days.

The resulting autoradiogram shows 5 positive colonies (clones) which can be used for further processing, one of which received the designation pML350.

B. Construction of plasmid pBH109

As plasmid pML350 originates from plasmid pIN-III-ompA-2 including a multi-cloning linker (EcoRI, HindIII, BamHI sites) it contains 12 additional base pairs in front of the mature hirudin gene coding for Ala, Gln, Phe, Met. To get mature desulphatohirudin expressed these 12 base pairs are looped out by in vitro mutagenesis making use of a 27 mer oligonucleotide.

a) Preparation of pML350/XbaI/BamHI (SI)

5 μg of plasmid pML350 are digested with the endonucleases XbaI and BamHI. The larger of the two XbaI-BamHI fragments (SI) is isolated by gel elution after electrophoresis on agarose and dissolved in 1 mM Tris-HCl pH 7.5, 0.1 mM EDTA.

b) Preparation of pML350/PvuI (SII)

5 μg of plasmid pML350 are digested with the endonuclease PvuI. The linearized DNA pML350/PvuI is subsequently digested with 3 units of intestinal alcaline phosphatase (Boehringer) for 30 min at 37° C. The enzyme is inactivated by heating the solution for 60 min at 65° C. The linear pML350/PvuI (SII) DNA is isolated by gel elution after electrophoresis on agarose and dissolved in 1 mM Tris-HCl pH 7.5, 0.1 mM EDTA.

c) Preparation of the oligonucleotide (27 mer) I27

In analogy to the procedure described in European Patent Application No. 168342 the following DNA fragment (designated I27) has been synthesized:

5′-GTA GCG CAG GCC GTT GTT TAC ACC GAC-3′    I27

The phosphorylation at the 5′ ends was done with [γ-$^{32}P$]-ATP and $T_4$ polynucleotide kinase (Boehringer) as described [Molecular Cloning, A Laboratory Manual (ed. T. Maniatis et al.), Cold Spring Harbor Lab. (1982), p. 125].

d) Construction of plasmid pBH109

0.3 μg each of SI DNA and of SII DNA are mixed with 40 pmol of the phosphorylated DNA fragment I27 in 27 μl of 1 mM Tris-HCl pH 7.5, 0.1 mM EDTA. To the mixture 3 μl of 10× polymerase-ligase buffer (1M NaCl, 65 mM Tris-HCl pH 7.5, 80 mM MgCl$_2$ and 10 mM β-mercaptoethanol) are added. This mixture is heated for 3 min in a boiling water bath to denature the DNA fragments. Subsequently, the mixture is gradually cooled (about 1° C./min) to 30° C. and incubated at this temperature for 30 min. Further the mixture is incubated at 4° C. for 30 min and afterwards for 10 min. in ice.

12 μl of the four deoxyribonucleotide phosphates (7.5 mM each), 6 μl of 10 mM ATP, 6 μl of T$_4$ DNA ligase (2.5 U/μl) and 1.2 μl of Klenow DNA polymerase (Boehringer, 5 U/μl) are added and the DNA mixture (total volume 55 μl) is incubated for 16 h at 12.5° C.

The DNA mixture is digested with 2 units of endonuclease EcoRI for 1 h at 37° C. in order to destroy unchanged starting plasmid pML350. With this procedure, plasmid pBH109 is formed. Plasmid pBH109 contains the lpp promoter and the lac promoter/operator operably linked to the ompA-2 signal sequence linked in frame to the gene coding for mature desulphato-hirudin.

e) Transformation of E. coli HB101 with plasmid pBH109

The transformation with calcium treated *E. coli* HB101 cells is done as described above. The total reaction mixture used is 55 μl.

f) Screening of the colonies which contain plasmid pBH109

100 transformed colonies are cultivated, from each colony plasmid DNA is prepared and digested with EcoRI. All plasmid DNAs, which are not digestable with EcoRI are potent plasmids pBH109 which is lacking the EcoRI site.

Two positive identical colonies have been identified. One of them is selected and designated pBH109.

The correct sequence of the F$_1$-F$_2$-DNA following the ompA-2 leader sequence is confirmed by sequence analysis.

C. Mutation of the residue Lys27 of hirudin to Asn27 using single stranded M13mp19/hirudin.

| coding strand of hirudin | 24 Gln | 26 Gly | 28 Asn | 30 <u>Lys</u> | Cys | Ile | Leu |
|---|---|---|---|---|---|---|---|
| | 5'CAG | GGT | AAC | <u>AAA</u> | TGC | ATC | CTG 3' |
| mutagenic primer 1 | 3'GTC | CCA | TTG | <u>TTA</u> | ACG | TAG | GAC 5' |
| mutated coding strand | 5'CAG | GGT | AAC | <u>AAT</u> | TGC | ATC | CTG 3' |
| | Gln | Gly | Asn | <u>Asn</u> | Cys | Ile | Leu |

Mutagenic primers are synthesised using the phosphoramidite method [M. H. Caruthers, in Chemical and Enzymatic Synthesis of Gene Fragments (H. G. Gassen and A. Lang, Eds.) Verlag Chemie, Weinheim, Federal Republic of Germany] on an Applied Biosystems (Model 380B) synthesiser.

I. Preparation of M13mp19/hirudin

XbaI-BamHI cut M13mp19 DNA

To 5 μl M13mp19 double stranded DNA (ds-DNA; 0.1 μg/ml; BRL) are added 2 μl React 2 (500 mM Tris-HCl, pH 8.0; 100 mM MgCl$_2$, 500 mM NaCl) (BRL), 1 μl XbaI (10 U/μl), 0.5 μl BamHI (10 U/μl) and 12 μl H$_2$O. After incubation at 37° C. for 1.5 h, 0.5 μl BamHI, 2.5 μl React 3 (500 mM Tris-HCl, pH 8.0; 100 mM MgCl$_2$; 1000 mM NaCl) (BRL), and 2 μl H$_2$O are added and incubation is continued at 37° C. for 1 h. The volume is made up to 100 μl with H$_2$O. The ds-DNA is isolated by phenol extraction and ethanol precipitation, and dissolved in 30 μl of TE buffer (Tris-HCl 10 mM, EDTA 1 mM, pH 8.0).

Insert DNA

Five μg of the plasmid pBH109 are cut with XbaI and BamHI as described above and the digest is electrophoresed for 3 h at 150 volt using a 3.5% polyacrylamide gel with 1× TBE buffer (10× TBE buffer: 108 g Tris, 55 g boric acid, 9.3 g EDTA•2H$_2$O/l). The XbaI-BamHI fragment containing the hirudin gene (250 bp) is visualised under UV light after immersing the gel in 400 ml 1× TBE buffer containing 10 μl of ethidium bromide solution (10 μg/ml in water). The part of the gel containing the restriction fragment is cut from the gel and placed in a dialysis bag with 500 μl of 0.5× TBE, and the DNA is electroeluted in a BIO-RAD minigel electrophoresis apparatus using 0.5× TBE as the running buffer at 170 volt for 30 min. The DNA is loaded onto an Elutip-d column (Schleicher & Schull) equilibrated with 0.5× TBE. The column is washed with 2 ml of 0.5× TBE and the DNA is eluted with 1M NaCl in 0.5× TBE (1 ml). The DNA is precipitated with ethanol and redissolved in 10 μl of TE buffer.

Ligation of XbaI-BamHI hirudin insert into M13mp19 and preparation of single stranded DNA.

Five μl XbaI-BamHI hirudin insert, 2 μl XbaI-BamHI cut M13mp19, 1 μl 10× ligase buffer (50 mM Tris-HCl, pH 7.5, 10 mM MgCl$_2$, 10 mM dithiothreitol), 1 μl ATP, 1.5 μl T4 DNA ligase (BRL; 1 U/μl) are mixed and incubated overnight at 14° C. Five μl of ligation mixture are used to transform *E. coli* JM101 competent cells according to the method of J. Messing [Methods in Enzymology 101, 21–78 (1983)]. Twelve clear plaques are picked and single stranded DNA (ss-DNA) is prepared from each plaque as described by J. Messing (supra). The DNA designated M13mp19/hirudin is redissolved in 50 μl of TE buffer (0.1–0.5 μg/μl).

II. Site-directed mutagenesis

Phosphorylation of mutagenic primer 200 pmol (23 μl) of mutagenic primer 1 (see above) is phosphorylated by adding 3 μl 10× kinase buffer (1M Tris-HCl, 0.1M MgCl$_2$, 0.1M dithiothreitol, pH 8.3) 3 μl 10 mM ATP and 1 μl T4 polynucleotide kinase (BRL, 10 U/μl). After incubation at 37° C. for 1 h, the reaction is stopped by heating at 65° C. for 10 min.

Annealing of the mutagenic primer 1 to the single-stranded M13mp19/hirudin template.

Six μl (0.5 μg) of single-stranded M13mp19/hirudin is incubated with 3 μl (20 pmol) of the phosphorylated mutagenic oligodeoxyribonucleotide (6.6 pmol/μl) and 1 μl buffer A (0.2M Tris-HCl, pH 7.5, 0.1M MgCl$_2$, 0.5M NaCl, 0.01M DTT) at 70° C. for 5 min, and cooled slowly to room temperature over 30 min.

Extension-ligation reaction

To the above annealed mix is added 1 μl buffer B (0.2M Tris-HCl, pH 7.5, 0.1M MgCl$_2$, 0.01M DTT), 1 μl 10 mM ATP, 4 μl 2 mM dNTP mixture, 5 μl T4 DNA polymerase (Boehringer, 1 U/μl), 5 μl T4 DNA ligase (BRL, 1 U/μl). This mixture is incubated at 16° C. for 3 h. The reaction is stopped by incubating at 65° C. for 10 min.

Transformation and preparation of single-stranded mutant DNA

The ligation mixture is diluted 1:20 with sterile H₂O, and 1 μl, 5 μl, as well as 1 μl undiluted ligation mixture is used to transform competent *E. coli* BMH 71-81 mut S cells [B. Kramer, W. Kramer and H.-J. Fritz, Cell 38, 879-887 (1984)]. The cells are plated out as described in the "M13 cloning and sequencing Handbook" (published by Amersham). Twelve colourless plaques are picked and ss-DNA is prepared as described above.

Screening of single-stranded DNA for mutant

To screen for mutated single-stranded DNA, each of the 12 ss-DNA samples is sequenced by the dideoxynucleotide chain termination method [F. Sanger, S. Nickler and A. R. Coulson, Proc. Natl. Acad. Sci. USA 74, 5463-5467 (1977)]. Initially, only the dideoxynucleotide complementary to the expected mutated base is used in the reaction. Subsequently, the ss-DNA from several positive mutants are sequenced to establish the full DNA sequence of the mutant using T7 DNA polymerase (Sequenase, USB) following the method of Tabor and Richardson [Proc. Natl. Acad. Sci. USA 84, 4767-4771 (1987)]. The expected base change encoding Lys—>Asn mutation at position 27 of the recombinant hirudin are observed in the DNA sequence. The phage DNA having the expected sequence is designated M13mp19/hirudin K27N.

Preparation of replicative form (RF) DNA from single-stranded M13mp19/hirudin K27N phage DNA.

Competent *E. coli* JM101 cells are transformed with 10-20 ng of single-stranded hirudin K27N mutant DNA and ds-DNA is prepared as described in the "M13 cloning and sequencing Handbook" (published by Amersham). A yield of 40-50 μg of ds-DNA is obtained from 100 ml of culture.

Isolation of mutant hirudin XbaI-BamHI insert

The mutated hirudin XbaI-BamHI insert is cut out of 25 μg of the ds-DNA and purified as described in section IB. The DNA is dissolved in 20 μl of sterile water.

Preparation of XbaI-BamHI cut pIN-III-ompA-2 vector DNA

A digest of approximately 1.5 μg pIN-III-ompA-2 plasmid is made by adding 6 μl React 2 buffer (BRL), 2 μl (20 Units) XbaI, 1 μl BamHI (10 Units), 1 μl EcoRI (10 Units) and 37 μl H₂O (total volume 50 μl), and incubation for 3 h at 37° C. 1 μl (10 Units) BamHI, 1 μl (10 Units) EcoRI, 5 μl React 3 (BRL) and 12 μl H₂O are added and incubation continued for 1 h at 37° C.

Ligation of mutant hirudin K27N XbaI-BamHI insert DNA into XbaI-BamHI cut pIN-III-ompA-2 plasmid Nine μl hirudin K27N XbaI-BamHI insert DNA, 2 μl XbaI-BamHI cut pIN-III-ompA-2 vector DNA, 3 μl 10× ligation buffer (BRL) and 1 μl (1 U/μl) T4 DNA ligase (BRL) are mixed and incubated at 14° C. for 16-20 h.

III. Expression of mutant [Asn$^{27}$]-desulfato hirudin in *E. coli* JM101.

Transfection into E. coli strain JM101

Five μl of ligation mixture is used to transform 0.3 ml of *E. coli* JM101 competent cells according to the method of J. Messing (supra). Three ml of 2×YT/Ampicillin (50 μg ampicillin/ml 2×YT) is added to the sample and the cells allowed to grow at room temperature for 1 h. A 1 ml sample of the culture is then taken and poured onto an LB/Ampicillin (50 μg ampicillin/ml LB-agar) plate and grown overnight at 37° C. The transforming plasmid DNA is referred to as pIN-III-ompA-2/HIR-K27N.

Selection of [Asn$^{27}$]-desulfato hirudin expressing colonies

Ten bacterial colonies from the LB/Ampicillin plates are picked and grown separately for 5 h at 37° C. in 5 ml LB/Ampicillin (50 μg Ampicillin/ml LB). 1 ml samples are taken from each culture tube and the cells recovered by centrifugation (3000×g for 5 min). Each sample of cells is osmotically shocked by treatment with 100 μl of 10 mM Tris-HCl, pH 8.1 for 30 min at 0° C. to release the material in the periplasmic space of the bacteria. The cells are removed by centrifugation as before, and the supernatant is tested for hirudin activity. The sample which gives the highest inhibitory activity is selected for batch culture.

Batch culture and isolation of [Asn$^{27}$]-desulfato hirudin

The remaining quantity (4 ml) of cells from the most active sample is used to inoculate 1 l of LB/Ampicillin (50 μg Ampicillin/ml LB). The culture is grown overnight at 37° C., and the cells are recovered by centrifugation (3000×g for 15 min.). The cell pellet is osmotically shocked by resuspension in 50 ml of 10 mM Tris-HCl, pH 8.1 at 0° C. for 1 h. The cells are removed from the periplasmic fraction by centrifugation at 6000×g for 10 min.

Purification of [Asn$^{27}$]-desulfato hirudin

The pH of the periplasmic fraction is adjusted to 6.5 with 0.1M HCl and filtered through a 0.45 μm filter (Nalgene). The protein is loaded onto a Mono-Q column FPLC system (Fast Protein Liquid Chromatography, Pharmacia-LKB), equilibrated with 50 mM bis-Tris-HCl buffer pH 6.5. The desulfato hirudin mutant is eluted from the column using a linear salt gradient of 0-300 mM NaCl in bis-Tris-HCl pH 6.5 over 45 min. 0.8 ml fractions of the column eluate are collected and tested for hirudin activity as described above. The desulfato hirudin mutant-containing fractions are pooled, filtered as above and chromatographed on a Millipore-Waters HPLC system using a Brownlee Labs C8 reversed-phase HPLC column equilibrated with 0.09% (v/v) trifluoroacetic acid in H₂O. The hirudin mutant is eluted from the column with a linear gradient of 7 to 28% (v/v) acetonitrile in 0.09% (v/v) trifluoroacetic acid in H₂O. [Asn$^{27}$]-desulfato hirudin having a purity of about or more than 98% elutes as a single peak at 28 min.

D. Mutation of the residue Lys 27 of hirudin to Gln 27, and of the residue Lys 47 to Arg 47

A: Mutation of Lys 27 to Gln 27

```
                                27
coding          Gln  Gly  Asn  Lys  Cys  Ile  Leu
strand of       5'CAG GGT AAC AAA TGC ATC CTG 3'
hirudin mutagenic       3'GTC CCA TTG GTT ACG TAG GAC 5'
primer 2A mutated         5'CAG GGT AAC CAA TGC ATC CTG 3'
coding          Gln  Gly  Asn  Gln  Cys  Ile  Leu
strand
```

B: Mutation of Lys 47 to Arg 47

```
                            47
coding          Gly  Thr  Pro  Lys  Pro  Gln  Ser
strand of       5'GGT ACC CCG AAA CCG CAG TCT 3'
hirudin mutagenic       3'CCA TGG GGC TCT GGC GTC AGA 5'
primer 2B mutated         5'GGT ACC CCG AGA CCG CAG TCT 3'
coding          Gly  Thr  Pro  Arg  Pro  Gln  Ser
strand
```

The procedures given above are repeated using mutagenic primers 2A and B to obtain and characterize the desired mutant protein in which Lys 27 is replaced by Gln 27 and Lys 47 by Arg 47. The transforming plasmid DNA is referred to as pIN-III-ompA-2/HIR-K27Q, K47R. The mutant is designated [Gln$^{27}$,Arg$^{47}$]-desulfato hirudin.

E. Mutation of the residue Lys 27 of hirudin to Gln 27, the residue Lys 36 to Gln 36, and of the residue Lys 47 to Arg 47.

a: Mutation of Lys 36 to Gln 36

```
                 34   35        38
coding strand   Asp  Gly  Glu  Lys  Asn  Gln  Cys
of hirudin      5' GAC GGT GAA AAA AAC CAG TGC 3' mutagenic       3' CTG CCA CTT GTT TTG GTC ACG 5'
primer 3
```

-continued
```
mutated         5' GAC GGT GAA CAA AAC CAG TGC 3'
coding strand   Asp  Gly  Glu  Gln  Asn  Gln  Cys
``` b: Mutation of Lys 27 to Gln 27

The mutation of Lys 27 to Gln 27 is performed according to D (above).

c: Mutation of Lys 47 to Arg 47

The mutation of Lys 47 to Arg 47 is performed according to D (above).

The procedures given above are repeated using mutagenic primers 2A, 3 and 2B to obtain and characterize the desired mutant protein in which Lys 27 is replaced by Gln 27, Lys 36 is replaced by Gln 36 and Lys 47 is replaced by Arg 47. The transforming plasmid DNA is referred to as pIN-III-ompA-2/HIR-K27Q,K36Q,K47R. The mutant is designated [Gln$^{27}$,Gln$^{36}$,Arg$^{47}$]-desulfato hirudin.

F. Extension of the N-terminus of [Gln$^{27}$,Arg$^{47}$]-desulfato hirudin with a methionine residue

```
                               1        3        5
coding strand   signal seq.    Val Val Tyr Thr Asp Cys
of hirudin      5' GCG CAG GCC ... GTT GTT TAC ACC GAC TGC 3' mutagenic       3' CGC GTC CGG TAC CAA CAA ATG TGG CTG ACG 5'
primer 4 mutated         5' GCG CAG GCC ATG GTT GTT TAC ACC GAC TGC 3'
coding strand   signal seq.    Met Val Val Tyr Thr Asp Cys
```

The procedures given above are repeated using mutagenic primers 2A, 2B and 4 to obtain and characterize the desired mutant protein in which the N-terminus of [Gln$^{27}$,Arg$^{47}$]-desulfato hirudin is extended by Met. The protein is designated methionyl-[Gln$^{27}$,Arg$^{47}$]-desulfato hirudin.

G. Mutation of the residues Glu 57,58,61,62 of hirudin to Gln 57,58,61,62

```
                          56        58        60        62        64
coding strand   Gly  Asp  Phe  Glu  Glu  Ile  Pro  Glu  Glu  Tyr  Leu  Gln
of hirudin      5' GTT GAC TTC GAA GAA ATC CCG GAA GAA TAC CTG CAG 3' mutagenic       3' CCA CTG AAG GTT GTT TAG GGC GTT GTT ATG GAC GTC 5'
primer 5 mutated         5' GGT GAC TTC CAA CAA ATC CCG CAA CAA TAC CTG CAG 3'
coding strand   Gly  Gly  Phe  Gln  Gln  Ile  Pro  Gln  Gln  Tyr  Leu  Gln
```

The procedures given above are repeated using mutagenic primer 5 to obtain and characterize the desired mutant protein in which Glu 57,58,61,62 are replaced by Gln 57,58,61,62. The mutant is designated [Gln$^{57,58,61,62}$]-desulfato hirudin.

H. Construction of a yeast expression plasmid coding for [Pro$^{66}$]-desulfato hirudin The DNA sequence coding for desulfato hirudin is extended by the oligonucleotide CCA, which codes for proline. The resulting new desulfato hirudin is expressed in yeast. It contains 66 aminoacids with a proline at its C-terminal end. This polypeptide is referred to as [Pro$^{66}$]-desulfato hirudin.

Yeast expression plasmid pJDB207/GAPFL-HIR (see FIG. 4; European patent application No. 225633) is digested with restriction endonucleases SalI and EcoRI. The 478 bp SalI-EcoRI fragment is separated on a 0.8% preparative agarose gel in TBE buffer (90 mM Tris-base, 90 mM boric acid, 2.5 mM EDTA pH 8.3). The ethidiumbromide-stained fragment is isolated from the gel. The DNA is electroeluted in 0.2×TBE buffer for 45 min at 100 mA and purified by DE52 (Whatman) ion exchange chromatography. The DNA is eluted from the DE52 column with a high salt buffer (1.5M NaCl, 10 mM Tris-HCl pH 8.0, 1 mM EDTA), precipitated with ethanol and redissolved in $H_2O$ at a concentration of 0.1 pmoles/μl. The 478 bp SalI-EcoRI fragment contains the SalI-BamHI sequence of pBR322 fused to the BglII-EcoRI GAPFL promoter fragment.

Plasmid pJDB207/GAPFL-HIR is digested with BamHI and SalI. The large, 6.7 kb vector fragment is isolated as described above. The small, 740 bp SalI-BamHI fragment is also isolated. It contains the sequence of the 478 bp SalI-EcoRI fragment (see above) in addition to the PH05 signal sequence fused in frame to the coding sequence of desulfato hirudin. The 740 bp fragment is digested with AsuII. The DNA is extracted with phenol/chloroform, precipitated with ethanol and redissolved in $H_2O$.

A synthetic oligodeoxynucleotide of the formula

```
                                     Pro
(1) 5'-CGAAGAAATCCCGGAAGAATACCTGCAGCCATAG    -3'
(2) 3'-   TTCTTTAGGGCCTTCTTATGGACGTCGGTATCCTAG -5'
``` is kinased in 40 μl of 60 mM Tris-HCl pH 7.5, 10 mM $MgCl_2$, 5 mM DTT, 0.5 mM ATP and 27 U of T4 polynucleotide kinase (Boehringer) for 45 min at 37° C. The reaction mixtures for oligonucleotides (1) and (2) are combined. The mixture is heated for 10 min at 75° C. and allowed to cool to room temperature. The annealed oligonucleotide linker (1+2) is stored at −20° C.

0.85 μg (3.8 pmoles) of the AsuII digested DNA are incubated for 16 h at 15° C. with a 100 fold excess of the kinased and annealed oligonucleotide linker over DNA ends in 150 μl of 60 mM Tris-HCl pH 7.5, 10 mM $MgCl_2$, 5 mM DTT, 3.5 mM ATP and 1200 U of T4 DNA ligase (Biolabs). After inactivation of the T4 DNA ligase for 10 min at 85° C. the excess linkers are removed by precipitation of the DNA in the presence of 10 mM EDTA, 300 mM sodium acetate pH 6.0 and 0.54 volumes of isopropanol. The DNA is digested with EcoRI and BamHI. The resulting fragments are separated on a 2% preparative agarose gel in TBE buffer. The 262 bp fragment is recovered from the gel by electroelution and ethanol precipitation. The DNA is resuspended at a concentration of 0.1 pmoles/μl. The EcoRI-BamHI fragment contains the coding sequence of desulfato hirudin with the additional CCA triplet coding for Pro 66.

Three DNA fragments, isolated as described above, are ligated in the following reaction: 0.2 pmoles of the 478 bp SalI-EcoRI fragment, 0.2 pmoles of the 262 bp EcoRI-BamHI fragment and 0.1 pmoles of the 6.7 kb vector fragment are ligated in 10 μl of 60 mM Tris-HCl pH 7.5, 10 mM $MgCl_2$, 5 mM DTT, 1 mM ATP and 200 U of T4 DNA ligase for 6 h at 15° C. A one μl aliquot of the ligation mixture is added to 100 μl of calcium-treated, transformation competent *E. coli* HB101 cells.

12 transformed, ampicillin-resistant colonies are grown in LB medium containing 100 mg/l of ampicillin. Plasmid DNA is prepared [Holmes et al., Anal. Biochem. 114 (1981), 193] and analysed by BamHI, EcoRI double digests. The presence of the mutation in the DNA is confirmed by DNA sequencing [Sanger et al., Proc. Natl. Acad. Sci. USA 74 (1977) 5463]. One clone with the CCA codon in the hirudin structural gene is referred to as pJDB207/GAPFL-HIR (Pro 66).

I. Mutation of the residues Val 1,2 of hirudin to Ile 1,2

```
                                           1           3         5
coding strand      signal seq.             Val Val   Tyr Thr Asp Cys
of hirudin         5' GCG CAG GCC          GTT GTT   TAC ACC GAC TGC 3' mutagenic primer 6 3' CGC GTC CGG          TAA TAA   ATG TGG CTG AGC 5' mutated coding     5' GCG CAG GCC          ATT ATT   TAC ACC GAC TGC 3'
strand             signal seq.             Ile Ile   Tyr Thr Asp Cys
```

The procedures given above are repeated using mutagenic primer 6 to obtain and characterize the desired mutant protein in which the N-terminal amino acids Val 1,2 are replaced by Ile 1,2. The mutant is designated [Ile$^{1,2}$]-desulfato hirudin.

J. Mutation of the residues Val 1 of hirudin to Gly 1

```
                                           1           3         5
coding strand      signal seq.             Val Val   Tyr Thr Asp Cys
of hirudin         5' GCG CAG GCC          GTT GTT   TAC ACC GAC TGC 3' mutagenic primer 7 3' CGC GTC CGG          CCA CAA   ATG TGG CTG ACG 5' mutated coding     5' GCG CAG GCC          GGT GTT   TAC ACC GAC TGC 3'
strand             signal seq.             Gly Val   Tyr Thr Asp Cys
```

The procedures given above are repeated using mutagenic primer 7 to obtain and characterize the desired mutant protein in which the N-terminal amino acid Val 1 is replaced by Gly 1. The mutant is designated [Gly$^1$]-desulfato hirudin.

In an analogous manner applying the procedures detailed in Example 3 any other desired mutant of desulfato hirudin HV1, hirudin HV2 and hirudin PA can be produced.

EXAMPLE 4

Pharmaceutical composition for parenteral administration and application

The pharmaceutical composition consists of seven vials each containing 10 mg lyophilised activator t-PA and 300 mg dextrose and an eighth vial containing 30 mg of lyophilised desulfato hirudin HV1 and 100 mg dextrose.

A solution for parenteral administration of t-PA is prepared by dissolving the contents of each of the seven vials in one 10 ml ampoule of sterile pyrogene-free solvent containing 100 mM ammonium acetate buffer, adjusted to pH 4 with acetic acid.

A solution for parenteral administration of desulfato hirudin is prepared by dissolving the contents of the vials in 3 ml of sterile 0.9% sodium chloride solution.

10% of the total plasminogen activator dosis (i.e. 7 mg t-PA) in 7 ml buffer and 30 mg desulfato hirudin in 3 ml buffer are aspirated into a sterile syringe containing 10 ml sterile 0.9% sodium chloride solution and intravenously given as an initial loading dose over 5 min. The remaining 63 mg of t-PA are injected into a 250 ml bottle of sterile 0.9% sodium chloride solution and then intravenously infused over 90 min to achieve opening of the occluded vessel.

Alternatively, 7 mg of t-PA (7 ml) and 10 mg of desulfato hirudin (1 ml) dissolved as described (supra) are given as a bolus dosis over 5 min. The remaining 63 mg of t-PA and 20 mg of desulfato hirudin are infused over 90 min in a total volume of 315 ml 0.9% sodium chloride solution.

Instead of t-PA it is also possible to use the same amount of another plasminogen activator mentioned hereinbefore, such as scu-PA or a u-PA/t-PA hybrid plasminogen activator. Analogously, instead of desulfato hirudin HV1 it is also possible to use the same amount of another hirudin mentioned hereinbefore, such as hirudin PA or a mutant of desulfato hirudin HV1.

We claim:

1. A pharmaceutical composition comprising in separate unit dosage forms as component A a plasminogen activator and as component B hirudin, together with pharmaceutically acceptable carriers.

2. A pharmaceutical composition according to claim 1 comprising as component A a plasminogen activator in the single chain form.

3. A pharmaceutical composition according to claim 1 comprising as component A a plasminogen activator selected from the group consisting of u-PA and t-PA including glycoylated, partially glycosylated or unglycosylated forms thereof, a u-PA/t-PA hybrid plasminogen activator and mutants and fragments thereof retaining the fibrinolytic activity.

4. A pharmaceutical composition according to claim 1 comprising as component A a plasminogen activator of the formula

| | | | | | | | | | | | | | | | |
|---|---|---|---|---|---|---|---|---|---|---|---|---|---|---|---|
| | | | | | | | Ser | Asn | Glu | Leu | His | Gln | Val | | (1) |
| Pro | Ser | Asn | Cys | Asp | Cys | Leu | Asn | Gly | Gly | Thr | Cys | Val | Ser | Asn | |
| Lys | Tyr | Phe | Ser | Asn | Ile | His | Trp | Cys | Asn | Cys | Pro | Lys | Lys | Phe | |
| Gly | Gly | Gln | His | Cys | Glu | Ile | Asp | Lys | Ser | Lys | Thr | Cys | Tyr | Glu | |
| Gly | Asn | Gly | His | Phe | Tyr | Arg | Gly | Lys | Ala | Ser | Thr | Asp | Thr | Met | |
| Gly | Arg | Pro | Cys | Leu | Pro | Trp | Asn | Ser | Ala | Thr | Val | Leu | Gln | Gln | |
| Thr | Tyr | His | Ala | His | Arg | Ser | Asp | Ala | Leu | Gln | Leu | Gly | Leu | Gly | |
| Lys | His | Asn | Tyr | Cys | Arg | Asn | Pro | Asp | Asn | Arg | Arg | Arg | Pro | Trp | |
| Cys | Tyr | Val | Gln | Val | Gly | Leu | Lys | Pro | Leu | Val | Gln | Glu | Cys | Met | |
| Val | His | Asp | Cys | Ala | Asp | Gly | $X_1$ | $X_2$ | Pro | Ser | Ser | Pro | Pro | Glu | |
| Glu | Leu | Lys | Phe | Gln | Cys | Gly | Gln | Lys | Thr | Leu | Arg | Pro | $Y_1$ | $Y_2$ | |
| $Y_3$ | Ile | Ile | Gly | Gly | Glu | Phe | Thr | Thr | Ile | Glu | Asn | Gln | Pro | Trp | |
| Phe | Ala | Ala | Ile | Tyr | Arg | Arg | His | Arg | Gly | Gly | Ser | Val | Thr | Tyr | |
| Val | Cys | Gly | Gly | Ser | Leu | Ile | Ser | Pro | Cys | Trp | Val | Ile | Ser | Ala | |
| Thr | His | Cys | Phe | Ile | Asp | Tyr | Pro | Lys | Lys | Glu | Asp | Tyr | Ile | Val | |
| Tyr | Leu | Gly | Arg | Ser | Arg | Leu | Asn | Ser | Asn | Thr | Gln | Gly | Glu | Met | |
| Lys | Phe | Glu | Val | Glu | Asn | Leu | Ile | Leu | His | Lys | Asp | Tyr | Ser | Ala | |
| Asp | Thr | Leu | Ala | His | His | Asn | Asp | Ile | Ala | Leu | Leu | Lys | Ile | Arg | |
| Ser | Lys | Glu | Gly | Arg | Cys | Ala | Gln | Pro | Ser | Arg | Thr | Ile | Gln | Thr | |
| Ile | Cys | Leu | Pro | Ser | Met | Tyr | Asn | Asp | Pro | Gln | Phe | Gly | Thr | Ser | |
| Cys | Glu | Ile | Thr | Gly | Phe | Gly | Lys | Glu | $Z_1$ | Ser | $Z_2$ | Asp | Tyr | Leu | |
| Tyr | Pro | Glu | Gln | Leu | Lys | Met | Thr | Val | Val | Lys | Leu | Ile | Ser | His | |
| Arg | Glu | Cys | Gln | Gln | Pro | His | Tyr | Tyr | Gly | Ser | Glu | Val | Thr | Thr | |
| Lys | Met | Leu | Cys | Ala | Ala | Asp | Pro | Gln | Trp | Lys | Thr | Asp | Ser | Cys | |
| Gln | Gly | Asp | Ser | Gly | Gly | Pro | Leu | Val | Cys | Ser | Leu | Gln | Gly | Arg | |
| Met | Thr | Leu | Thr | Gly | Ile | Val | Ser | Trp | Gly | Arg | Gly | Cys | Ala | Leu | |
| Lys | Asp | Lys | Pro | Gly | Val | Tyr | Thr | Arg | Val | Ser | His | Phe | Leu | Pro | |
| Trp | Ile | Arg | Ser | His | Thr | Lys | Glu | Glu | Asn | Gly | Leu | Ala | Leu | | | in which $X_1$ and $X_2$ independently from each other represent Lys, an amino acid residue other than a basic amino acid residue or a chemical bond, $Y_1$ is Arg, an amino acid residue other than a basic amino acid residue or a chemical bond, $Y_2$ is Phe, an acidic amino acid residue or a chemical bond, $Y_3$ is Lys, an amino acid residue other than a basic amino acid residue or a chemical bond, $Z_1$ is Asn or is another amino acid residue, and $Z_2$ is Thr or another amino acid residue different from Ser.

5. A pharmaceutical composition according to claim 4 comprising as component A a plasminogen activator of the formula I in which $X_1$ is Lys, Gly or Ser, $X_2$ represents Lys, $Y_1$ is Arg, $Y_2$ is Phe, Asp or Glu, $Y_3$ is Lys, $Z_1$ is Asn or Gln and $Z_2$ is Thr.

6. A pharmaceutical composition according to claim 4 comprising as component A a plasminogen activator selected from the group consisting of scu-PA, [Gly[135]]-scu-PA, [Ser[135]]-scu-PA, [Asp[157]]-scu-PA, [Ser[135],Asp[157]]-scu-PA and [Gly[135],Asp[157]]-scu-Pa wherein Asn[302] is yeast specifically glycosylated, and [Gln[302]]-scu-PA, [Gly[135],Asp[157],Gln[302]]-scu-PA and [Ser[135],Asp[157],Gln[302]]-scu-PA.

7. A pharmaceutical composition according to claim 4 comprising as component A scu-PA.

8. A pharmaceutical composition according to claim 1 comprising as component A a plasminogen activator of the formula

| Ser | Tyr | Gln | Val | Ile | Cys | Arg | Asp | Glu | Lys | Thr | Gln | Met | Ile | Tyr | Gln | Gln | (II) |
|-----|-----|-----|-----|-----|-----|-----|-----|-----|-----|-----|-----|-----|-----|-----|-----|-----|------|
| His | Gln | Ser | Trp | Leu | Arg | Pro | Val | Leu | Arg | Ser | Asn | Arg | Val | Glu | Tyr | Cys | |
| Trp | Cys | Asn | Ser | Gly | Arg | Ala | Gln | Cys | His | Ser | Val | Pro | Val | Lys | Ser | Cys | |
| Ser | Glu | Pro | Arg | Cys | Phe | Asn | Gly | Gly | Thr | Cys | Gln | Gln | Ala | Leu | Tyr | Phe | |
| Ser | Asp | Phe | Val | Cys | Gln | Cys | Pro | Glu | Gly | Phe | Ala | Gly | Lys | Cys | Cys | Glu | |
| Ile | Asp | Thr | Arg | Ala | Thr | Cys | Tyr | Glu | Asp | Gln | Gly | Ile | Ser | Tyr | Arg | Gly | |
| Thr | Trp | Ser | Thr | Ala | Glu | Ser | Gly | Ala | Glu | Cys | Thr | Asn | Trp | $X_1$ | Ser | $Y_1$ | |
| Ala | Leu | Ala | Gln | Lys | Pro | Tyr | Ser | Gly | Arg | Arg | Pro | Asp | Ala | Ile | Arg | Leu | |
| Gly | Leu | Gly | Asn | His | Asn | Tyr | Cys | Arg | Asn | Pro | Asp | Arg | Asp | Ser | Lys | Pro | |
| Trp | Cys | Tyr | Val | Phe | Lys | Ala | Gly | Lys | Tyr | Ser | Ser | Glu | Phe | Cys | Ser | Thr | |
| Pro | Ala | Cys | Ser | Glu | Gly | Asn | Ser | Asp | Cys | Tyr | Phe | Gly | $X_2$ | Gly | $Y_2$ | Ala | |
| Tyr | Arg | Gly | Thr | His | Ser | Leu | Thr | Glu | Ser | Gly | Ala | Ser | Cys | Leu | Pro | Trp | |
| Asn | Ser | Met | Ile | Leu | Ile | Gly | Lys | Val | Tyr | Thr | Ala | Gln | Asn | Pro | Ser | Ala | |
| Gln | Ala | Leu | Gly | Leu | Gly | Lys | His | Asn | Tyr | Cys | Arg | Asn | Pro | Asp | Gly | Asp | |
| Ala | Lys | Pro | Trp | Cys | His | Val | Leu | Lys | Asn | Arg | Arg | Leu | Thr | Trp | Glu | Tyr | |
| Cys | Asp | Val | Pro | Ser | Cys | Ser | Thr | Cys | Gly | Leu | Arg | Gln | Tyr | Ser | Gln | Pro | |
| Gln | Phe | Arg | Ile | Lys | Gly | Gly | Leu | Phe | Ala | Asp | Ile | Ala | Ser | His | Pro | Trp | |
| Gln | Ala | Ala | Ile | Phe | Ala | Lys | His | Arg | Arg | Ser | Pro | Gly | Glu | Arg | Phe | Leu | |
| Cys | Gly | Gly | Ile | Leu | Ile | Ser | Ser | Cys | Trp | Ile | Leu | Ser | Ala | Ala | His | Cys | |
| Phe | Gln | Glu | Arg | Phe | Pro | Pro | His | His | Leu | Val | Ile | Leu | Gly | Arg | Thr | | |
| Tyr | Arg | Val | Val | Pro | Gly | Glu | Glu | Glu | Gln | Lys | Phe | Glu | Val | Glu | Lys | Tyr | |
| Ile | Val | His | Lys | Glu | Phe | Asp | Asp | Asp | Thr | Tyr | Asp | Asn | Asp | Ile | Ala | Leu | |
| Leu | Gln | Leu | Lys | Ser | Asp | Ser | Ser | Arg | Cys | Ala | Gln | Glu | Ser | Ser | Val | Val | |
| Arg | Thr | Val | Cys | Leu | Pro | Pro | Ala | Asp | Leu | Gln | Leu | Pro | Asp | Trp | Thr | Glu | |
| Cys | Glu | Leu | Ser | Gly | Tyr | Gly | Lys | His | Glu | Ala | Leu | Ser | Pro | Phe | Tyr | Ser | |
| Glu | Arg | Leu | Lys | Glu | Ala | His | Val | Arg | Leu | Tyr | Pro | Ser | Ser | Arg | Cys | Thr | |
| Ser | Gln | His | Leu | Leu | $X_3$ | Arg | $Y_3$ | Val | Thr | Asp | Asn | Met | Leu | Cys | Ala | Gly | |
| Asp | Thr | Arg | Ser | Gly | Gly | Pro | Gln | Ala | Asn | Leu | His | Asp | Ala | Cys | Gln | Gly | |
| Asp | Ser | Gly | Gly | Pro | Leu | Val | Cys | Leu | Asn | Asp | Gly | Arg | Met | Thr | Leu | Val | |
| Gly | Ile | Ile | Ser | Trp | Gly | Leu | Gly | Cys | Gly | Gln | Lys | Asp | Val | Pro | Gly | Val | |
| Tyr | Thr | Lys | Val | Thr | Asn | Tyr | Leu | Asp | Trp | Ile | Arg | Asp | Asn | Met | Arg | Pro | | in which $X_1$, $X_2$ and $X_3$ each represent Asn or another genetically encoded amino acid, $Y_1$ and $Y_2$ each represent Ser or another genetically encoded amino acid other than Thr and $Y_3$ represents Thr or another genetically encoded amino acid other than Ser.

9. A pharmaceutical composition according to claim 8 comprising as component A a plasminogen activator of the formula II in which one, two or three of the radicals $X_1$, $X_2$ and $X_3$ represent Asn and the other(s) represent(s) an amino acid residue selected from Gln, Thr and Ser, $Y_1$ and $Y_2$ each represent Ser and $Y_3$ represents Thr, or in which $X_1$, $X_2$ and $X_3$ each represent Asn, one or two of the radicals $Y_1$ and $Y_2$ represent Ser and the other(s) is (are) selected from the group consisting of Ala and Asn and $Y_3$ represents Thr, or in which $X_1$, $X_2$ and $X_3$ each represent Asn, $Y_1$ and $Y_2$ each represent Ser and $Y_3$ is selected from the group consisting of Ala and Asn.

10. A pharmaceutical composition according to claim 8 comprising as component A a plasminogen activator selected from the group consisting of t-PA, [Asn$^{119}$]-t-PA, [Ala$^{186}$]-t-PA, [Ala$^{450}$]-t-PA, [Asn$^{119}$, Ala$^{186}$]-t-PA, [Asn$^{119}$, Ala$^{186}$, Asn$^{450}$]-t-PA and [Asn$^{119}$, Ala$^{186}$, Ala$^{450}$]-t-PA.

11. A pharmaceutical composition according to claim 8 comprising as component A t-PA.

12. A pharmaceutical composition according to claim 1 comprising as component A a mutant of a u-PA/t-PA hybrid plasminogen activator in which at least one of the N-glycosylation sites is modified such that glycosylation cannot take place at this site.

13. A pharmaceutical composition according to claim 1 comprising as component B a hirudin selected from the group consisting of hirudin variant HV1 having the formula

| Val | Val | Tyr | Thr | Asp | Cys | Thr | Glu | Ser | Gly | (III) |
|-----|-----|-----|-----|-----|-----|-----|-----|-----|-----|-------|
| Gln | Asn | Leu | Cys | Leu | Cys | Glu | Gly | Ser | Asn | |
| Val | Cys | Gly | Gln | Gly | Asn | Lys | Cys | Ile | Leu | |
| Gly | Ser | Asp | Gly | Glu | Lys | Asn | Gln | Cys | Val | |
| Thr | Gly | Glu | Gly | Thr | Pro | Lys | Pro | Gln | Ser | |
| His | Asn | Asp | Gly | Asp | Phe | Glu | Glu | Ile | Pro | |
| Glu | Glu | Tyr(W) | Leu | Gln | | | | | | | wherein W represents the phenolic hydroxy group of Tyr (desulfato hirudin HV1) or a group of the formula —O—SO$_3$H (hirudin HV1), hirudin variant HV2 having the formula

| Ile | Thr | Tyr | Thr | Asp | Cys | Thr | Glu | Ser | Gly | Gln | Asn | Leu | Cys | (IV) |
|-----|-----|-----|-----|-----|-----|-----|-----|-----|-----|-----|-----|-----|-----|------|
| Leu | Cys | Glu | Gly | Ser | Asn | Val | Cys | Gly | Lys | Gly | Asn | Lys | Cys | |
| Ile | Leu | Gly | Ser | Asn | Gly | Lys | Gly | Asn | Gln | Cys | Val | Thr | Gly | |
| Glu | Gly | Thr | Pro | Asn | Pro | Glu | Ser | His | Asn | Asn | Gly | Asp | Phe | |
| Glu | Glu | Ile | Pro | Glu | Glu | Tyr | Leu | Gln | | | | | | | and hirudin variant PA having the formula

| Ile | Thr | Tyr | Thr | Asp | Cys | Thr | Glu | Ser | Gly | Gln | Asn | Leu | Cys | (V) |
|-----|-----|-----|-----|-----|-----|-----|-----|-----|-----|-----|-----|-----|-----|-----|
| Leu | Cys | Glu | Gly | Ser | Asn | Val | Cys | Gly | Lys | Gly | Asn | Lys | Cys | |
| Ile | Leu | Gly | Ser | Gln | Gly | Lys | Asp | Asn | Gln | Cys | Val | Thr | Gly | |
| Glu | Gly | Thr | Pro | Lys | Pro | Gln | Ser | His | Asn | Gln | Gly | Asp | Phe | |
| Glu | Pro | Ile | Pro | Glu | Asp | Ala | Tyr | Asp | Glu | | | | | | or a mutant or a fragment of any of said hirudin variants retaining the antithrombotic activity.

14. A pharmaceutical composition according to claim 13 comprising as component B a hirudin selected from the group consisting of desulfato hirudin HV1, hirudin HV1, hirudin HV2 und hirudin PA.

15. A pharmaceutical composition according to claim 13 comprising as component B desulfato hirudin HV1.

16. A pharmaceutical composition according to claim 13 comprising as component B a hirudin selected from the group consisting of [Ile$^{1,2}$]-desulfato hirudin HV1, [Gly$^1$]-desulfato hirudin HV1, [Gln$^{57,58,61,62}$]-desulfato hirudin HV1, [Pro$^{66}$]-desulfato hirudin HV1, [Gln$^{27}$,Arg$^{47}$]-desulfato hirudin HV1, [Met$^0$,Gln$^{2-7}$,Arg$^{47}$]-desulfato hirudin HV1, [Gln$^{27}$,Gln$^{36}$,Arg$^{47}$]-desulfato hirudin HV1, [des-Val$^1$,Thr$^2$]-desulfato hirudin HV1 and [Lys$^{47}$]-hirudin HV2.

17. a pharmaceutical compsoition according to claim 1 comprising as component A a plasminogen activator selected from the group consisting of scu-PA, t-PA, [Ala$^{450}$]-t-PA, [Asn$^{119}$, Ala$^{186}$, Ala$^{450}$]-t-PA, [uPA(1-44)-tPA(176-527)], [tPA(1-49)-tPA(176-275)-uPA(159-411)] and [tPA(1-3)-tPA(176-275)-uPA(159-411)], and as component B desulfato hirudin HV1.

18. A pharmaceutical composition according to claim 1 wherein the ratio by weight of component A to component B is between 20:1 and 2:1.

19. A pharmaceutical composition according to claim 1 wherein the ratio by weight of component A to component B is between 5:1 and 2:1.

20. A pharmaceutical composition according to claim 1, wherein the plasminogen activator comprises a single-chain plasminogen activator comprising the human t-PA A chain linked in series to the human u-PA B chain.

21. A pharmaceutical composition according to claim 1, wherein the plasminogen activator comprises a single-chain plasminogen activator comprising the human u-PA A chain linked in series to the human t-PA B chain.

22. A pharmaceutical composition according to claim 1, wherein the plasminogen activator comprises a single-chain hybrid plasminogen activator wherein the amino acid segment of human u-PA following the u-PA kringle up to the u-PA activation site is replaced by the amino acid segment following the t-PA kringle 2 up to the t-PA activation site.

23. A pharmaceutical composition according to claim 1, wherein the plasminogen activator comprises a single chain plasminogen activator comprising the human t-PA kringle 2 domain linked in series with the human u-PA B-chain.

24. A pharmaceutical composition according to claim 1, wherein the plasminogen activator comprises a single chain plasminogen activator comprising the human t-PA finger domain linked in series with the human u-PA B-chain.

25. A pharmaceutical composition according to claim 1, wherein the plasminogen activator comprises a single chain plasminogen activator comprising the human t-PA finger and kringle 2 domains linked in series with the human u-PA B-chain.

26. A pharmaceutical composition according to claim 1, wherein the plasminogen activator comprises a single-chain plasminogen activator comprising the human t-PA finger, kringle 2 and growth factor domains linked in series to the human u-PA B chain.

27. A pharmaceutical composition according to claim 1, wherein the plasminogen activator comprises a single chain plasminogen activator comprising the human u-PA growth factor domain and t-PA kringle 2 domain linked in series with the human t-PA B-chain.

28. A pharmaceutical composition according to claim 1, wherein the plasminogen activator comprises a single chain plasminogen activator comprising the human u-PA growth factor domain and t-PA kringle 2 domain linked in series with the human u-PA B-chain.

29. A pharmaceutical composition according to claim 1, wherein the plasminogen activator comprises:
a) an A chain consisting essentially of the u-PA growth factor domain and t-PA kringle 2 domain; linked in series to
b) the B chain of t-PA.

30. A pharmaceutical composition according to claim 1, wherein the plasminogen activator comprises:
a) an A chain consisting essentially of the t-PA kringle 2 domain; linked in series to
b) the B chain of u-PA; wherein the junction between the A chain and the B chain occurs at the activation site.

31. A pharmaceutical composition according to claim 1, wherein the plasminogen activator comprises:
a) an A chain consisting essentially of the t-PA finger domain and the t-PA kringle 2 domain; linked in series to
b) the B chain of u-PA;
wherein the junction between the A chain and the B chain occurs at the activation site.

32. A pharmaceutical composition according to claim 1 comprising as component A a single-chain hybrid plasminogen activator selected from the group consisting of:
[uPA(1-44)-tPA(176-527)],
[tPA(1-49)-tPA(176-275)-uPA(159-411)], and
[tPA(1-3)-tPA(176-275)-uPA(159-411)].

33. A method of treating thrombosis or a disease caused by thrombosis in a mammal comprising
a) administering to said mammal an antithrombotically effective amount of hirudin and;
b) subsequently administering a fibrinolytically effective amount of a plasminogen activator; and, if desired,
c) administering an antithrombotically effective amount of hirudin so as to prevent the reocclusion of the opened vessels.

34. A method of treating thrombosis or a disease caused by thrombosis in a mammal comprising:
a) administering to said mammal an antithrombotically effective amount of hirudin and a fibrinolytically effective amount of a plasminogen activator, wherein about 5 to 20% of the total dose of plasminogen activator is administered with hirudin; and
b) subsequently administering the remaining quantity of plasminogen activator; and, if desired,
c) administering an antithrombotically effective amount of hirudin so as to prevent the reocclusion of the opened vessels.

* * * * *